(12) United States Patent
Sabelle et al.

(10) Patent No.: US 7,090,703 B2
(45) Date of Patent: Aug. 15, 2006

(54) PARA-PHENYLENEDIAMINE DERIVATIVES COMPRISING A CYCLIC DIAZA GROUP SUBSTITUTED WITH A CATIONIC RADICAL, AND USE OF THESE DERIVATIVES FOR DYEING KERATIN FIBERS

(75) Inventors: Stéphane Sabelle, Paris (FR); Alain Genet, Aulnay Sous Bois (FR); Madeleine Leduc, Paris (FR)

(73) Assignee: L'Oreal, Paris (FR)

( * ) Notice: Subject to any disclaimer, the term of this patent is extended or adjusted under 35 U.S.C. 154(b) by 222 days.

(21) Appl. No.: 10/807,162

(22) Filed: Mar. 24, 2004

(65) Prior Publication Data

Related U.S. Application Data

(60) Provisional application No. 60/467,123, filed on May 2, 2003.

(30) Foreign Application Priority Data

Mar. 24, 2003 (FR) .................................. 03 03548

(51) Int. Cl.
*A61K 7/13* (2006.01)
(52) U.S. Cl. .................. 8/405; 8/406; 8/410; 8/411; 8/421; 8/565; 8/570; 8/573; 8/574; 540/575; 544/394; 514/341

(58) Field of Classification Search ............... 8/405, 8/406, 410, 411, 421, 565, 570, 573, 574; 540/575; 544/394; 514/341
See application file for complete search history.

(56) References Cited

FOREIGN PATENT DOCUMENTS

| EP | 0 891 765 | 1/1999 |
| EP | 0 962 452 | 12/1999 |
| WO | WO 98/38175 | 9/1998 |
| WO | WO 03/014093 | 2/2003 |
| WO | WO 03/014093 A1 * | 2/2003 |

OTHER PUBLICATIONS

STIC Search Report, Mar. 22, 2006.*
Patent Abstracts of Japan, vol. 1999, No. 11, Jun. 15, 1999.

* cited by examiner

Primary Examiner—Eisa Elhilo
(74) Attorney, Agent, or Firm—Finnegan, Henderson, Farabow, Garrett & Dunner, L.L.P.

(57) ABSTRACT

The disclosure relates to novel para-phenylenediamine derivatives containing a cyclic diaza group, substituted with a cationic radical, as well as to the dye compositions comprising them, and to the method of dyeing keratin fibers using these compositions.

The present invention may make it possible to obtain a chromatic, strong, relatively unselective and fast coloration on keratin fibers.

40 Claims, No Drawings

PARA-PHENYLENEDIAMINE DERIVATIVES COMPRISING A CYCLIC DIAZA GROUP SUBSTITUTED WITH A CATIONIC RADICAL, AND USE OF THESE DERIVATIVES FOR DYEING KERATIN FIBERS

This application claims benefit of U.S. Provisional Application No. 60/467,123, filed May 2, 2003.

The present disclosure relates to novel para-phenylenediamine derivatives comprising a cyclic diaza group substituted with a cationic radical, to the dye compositions comprising at least one para-phenylenediamine as disclosed herein, and to a process for dyeing keratin fibers using these dye compositions.

It is known practice to dye keratin fibers, for instance, human hair, with dye compositions containing oxidation dye precursors, such as ortho- or para-phenylenediamines, ortho- or para-aminophenols, heterocyclic compounds such as diaminopyrazole derivatives, pyrazolo[1,5-a]pyrimidine derivatives, pyrimidine derivatives, pyridine derivatives, 5,6-dihydroxyindole derivatives and 5,6-dihydroxyindoline derivatives, which may also be referred to as oxidation bases. Oxidation dye precursors, or oxidation bases, are colorless or weakly colored compounds that, when combined with oxidizing products, can give rise to colored compounds and dyes by a process of oxidative condensation.

It is also known that the shades obtained with these oxidation bases may be varied by combining them with couplers or coloration modifiers, the latter being chosen from, for example, aromatic meta-diamines, meta-aminophenols, meta-hydroxyphenols and certain heterocyclic compounds such as, for example, pyrazolo[1,5-b]-1,2,4-triazole derivatives, pyrazolo[3,2-c]-1,2,4-triazole derivatives, pyrazolo[1,5-a]pyrimidine derivatives, pyridine derivatives, pyrazol-5-one derivatives, indoline derivatives and indole derivatives.

The variety of molecules that may be used as oxidation bases and couplers allows a wide range of colors to be obtained.

The "permanent" coloration obtained with these oxidation dyes should, moreover, satisfy a certain number of requirements. For instance, it should have no toxicological drawbacks, allow shades to be obtained in the desired intensity, and show good resistance to external agents such as light, bad weather, washing, permanent-waving, perspiration and rubbing.

The dyes should also allow white hairs to be covered. Additionally, the dyes should be as unselective as possible, i.e., they must produce the smallest possible color differences along the same length of keratin fiber, which may be differently sensitized (i.e., damaged) between its end and its root. They should also show good chemical stability in the formulations, and have a good toxicological profile.

In the field of hair dyeing, para-phenylenediamine and para-tolylenediamine are oxidation bases that are widely used. They give varied shades with oxidation couplers.

However, there is a need in the art for novel oxidation bases that have a better toxicological profile than para-phenylenediamine and para-tolylenediamine, while at the same time giving the hair excellent properties in terms of color intensity, variety of shades, color uniformity and fastness with respect to external agents.

It is already known to use para-phenylenediamine derivatives substituted with a pyrrolidine group as oxidation bases for dyeing keratin fibers as replacements for para-phenylene-diamine. For example, U.S. Pat. No. 5,851,237 describes the use of 1-(4-aminophenyl)pyrrolidine derivatives optionally substituted on the benzene nucleus. U.S. Pat. No. 5,993,491 proposes the use of N-(4-aminophenyl)-2-hydroxymethylpyrrolidine derivatives optionally substituted on the benzene nucleus and on the pyrrolidine heterocycle in position 4 with a hydroxyl radical.

Patent Application JP 11-158,048 teaches compositions containing at least one compound chosen from para-phenylene-diamine derivatives optionally substituted on the benzene nucleus, and one of the nitrogen atoms of which is included in a 5- to 7-membered carbon ring.

Publication DE 197 07 545 describes the use of para-phenylenediamine compounds in which one of the amino groups forms a diazacycloheptane, for dyeing keratin fibers.

However, the compounds described in the above mentioned references do not make it possible to give the hair a coloration that is equivalent in quality to that obtained with para-phenylenediamine or with para-tolylenediamine due to the lack of intensity and uniformity of color.

The present inventors, therefore, have developed novel dye compositions that may not have the drawbacks of the oxidation bases of the prior art. For example, the present inventors provide herein novel oxidation bases that simultaneously have a good toxicological profile and properties such that the dye compositions comprising them do not degrade keratin fibers, while at the same time being capable of generating colorations in varied shades that are, for example, strong, unselective and fast.

Thus, disclosed herein is a compound of formula (I), wherein the compound is a para-phenylenediamine derivative substituted with a cyclic diaza group, and addition salts thereof:

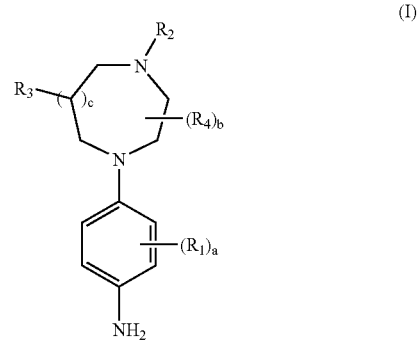

(I)

wherein
  a ranges from 0 to 4, it being understood that when a is greater than or equal to 2, then the radicals $R_1$ may be identical or different,
  b ranges from 0 to 4, it being understood that when b is greater than or equal to 2, then the radicals $R_4$ may be identical or different,
  c is equal to 0 or 1,
  $R_1$ may be chosen from halogen atoms; $C_1$–$C_8$ aliphatic and alicyclic, saturated and unsaturated, hydrocarbon-based chains wherein at least one carbon atom may be replaced with at least one entity chosen from oxygen, nitrogen, silicon and sulphur atoms and an $SO_2$ group; and an onium radical Z; with the proviso that the radical $R_1$ does not comprise a peroxide bond or diazo, nitro or nitroso radicals, $R_2$ comprises an onium radical Z, wherein an onium radical is a nitrogen-based quaternary radical, $R_3$ may be chosen from
- an alkyl radical;
- an alkenyl radical;
- an alkynyl radical;
- a hydroxyl radical;
- a hydroxyalkyl radical;
- an alkoxy radical;
- an alkoxyalkyl radical;
- an alkylcarbonyl radical;
- a hydroxyalkoxyalkyl radical;
- an amino radical;
- a monoalkylamino radical;
- a dialkylamino radical;
- an aminoalkyl radical;
- an aminoalkyl radical wherein the amine is monosubstituted or disubstituted with at least one radical chosen from alkyl, acetyl and hydroxyalkyl radicals;
- a hydroxyl radical;
- an aminoalkyl radical;
- a carboxyl radical;
- a carboxyalkyl radical;
- a carbamoyl radical;
- a carbamoylalkyl radical;
- an alkoxycarbonyl radical;
- a monoalkylaminocarbonyl radical;
- a dialkylaminocarbonyl radical;
- a monoalkylaminocarbonylalkyl radical; and
- a dialkylaminocarbonylalkyl radical;

$R_4$ may be chosen from
- an alkyl radical;
- an alkenyl radical;
- an alkynyl radical;
- a hydroxyalkyl radical;
- an alkoxyalkyl radical;
- an alkylcarbonyl radical;
- a hydroxyalkoxyalkyl radical;
- an aminoalkyl radical;
- an aminoalkyl radical wherein the amine is monosubstituted or disubstituted with at least one radical chosen from alkyl, acetyl and hydroxyalkyl radicals;
- a hydroxyl radical;
- a aminoalkyl radical;
- a carboxyl radical;
- a carboxyalkyl radical;
- a carbamoyl radical;
- a carbamoylalkyl radical;
- an alkoxycarbonyl radical;
- a monoalkylaminocarbonyl radical;
- a dialkylaminocarbonyl radical;
- a monoalkylaminocarbonylalkyl radical; and
- a dialkylaminocarbonylalkyl radical.

Also disclosed herein are the nitro derivatives of formula (I') included in the synthesis of the derivatives of formula (I) as presently disclosed.

Further disclosed herein is a dye composition comprising at least one para-phenylenediamine compound of formula (I) as an oxidation base.

Yet another aspect of the present disclosure is the use of the aforementioned composition for dyeing keratin fibers and the process for dyeing keratin fibers, for instance human keratin fibers such as hair, using the composition of the present disclosure.

The composition of the present disclosure, for example, makes it possible to obtain a chromatic, powerful, unselective and fast coloration of keratin fibers.

In the context of the present disclosure, an aliphatic hydrocarbon-based chain is a linear or branched chain that may contain unsaturations of the alkene or alkyne type. An alicyclic hydrocarbon-based chain is a saturated or unsaturated, branched chain not containing an aromatic cyclic structure.

The term "onium" means a nitrogen-based quaternary radical.

The compounds of formula (I) are para-phenylenediamines wherein one amine is included in a ring of 1,4-diazacycloheptane type, this ring also being referred to in the literature as 1,4-diazepane, or wherein one amine is included in a ring of 1,4-diazacyclohexane type, which is also referred to in the literature as 1,4-piperazine.

In formula (I) above, $R_1$ may be chosen from $C_1$–$C_4$ alkyl radicals, $C_1$–$C_4$ alkoxyalkyl radicals, $C_1$–$C_4$ hydroxyalkyl radicals, $C_1$–$C_4$ aminoalkyl radicals, $C_1$–$C_4$ alkoxy radicals, $C_1$–$C_4$ hydroxyalkoxy radicals, and $C_1$–$C_4$ carboxyalkyl radicals.

By way of non-limiting example, $R_1$ may be chosen from a chlorine atom, and from methyl, ethyl, isopropyl, vinyl, allyl, methoxymethyl, 1-hydroxyethyl, 1-carboxymethyl, 1-aminomethyl, 2-carboxyethyl, 2-hydroxyethyl, 3-hydroxypropyl, 1,2-dihydroxyethyl, 1-hydroxy-2-aminoethyl, 1-amino-2-hydroxyethyl, 1,2-diaminoethyl, methoxy, ethoxy, allyloxy and 2-hydroxyethyloxy radicals.

According to one aspect of the present disclosure, $R_1$ may be chosen from chlorine, bromine, and from $C_1$–$C_4$ alkyl, $C_1$–$C_4$ hydroxyalkyl, $C_1$–$C_4$ aminoalkyl, $C_1$–$C_4$ alkoxy and $C_1$–$C_4$ hydroxyalkoxy radicals. $R_1$ may, for instance, be chosen from methyl, hydroxymethyl, 2-hydroxyethyl, 1,2-dihydroxyethyl, methoxy, isopropyloxy and 2-hydroxyethoxy radicals.

In one embodiment, a may be equal to 0 or 1, for example, a may be 0.

In another embodiment, $R_2$ comprises an onium radical Z corresponding to formula (II)

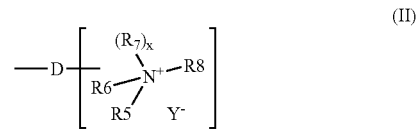

wherein

D is a linker arm chosen from a covalent bond and from linear and branched $C_1$–$C_{14}$ alkylene chains which may comprise at least one hetero atom chosen from oxygen, sulphur and nitrogen, and which may be substituted with at least one radical chosen from hydroxyl and amino radicals, and which may further comprise at least one carbonyl radical;

$R_8$, $R_5$ and $R_6$, which may be identical or different, may each be chosen from $C_1$–$C_{15}$ alkyl radicals; $C_1$–$C_6$ monohydroxyalkyl radicals; $C_2$–$C_6$ polyhydroxyalkyl radicals; $(C_1$–$C_6)$alkoxy$(C_1$–$C_6)$alkyl radicals; aryl radicals; benzyl radicals; $C_1$–$C_6$ carbamoylalkyl radicals; tri$(C_1$–$C_6)$alkylsilane$(C_1$–$C_6)$alkyl radicals; $C_1$–$C_6$ aminoalkyl radicals; $C_1$–$C_6$ aminoalkyl radicals wherein the amine is mono- or disubstituted with a radical chosen from $C_1$–$C_4$ alkyl, $(C_1$–$C_6)$alkylcarbonyl, carbamoyl and $(C_1$–$C_6)$alkylsulphonyl radicals; and quaternary ammonium radicals;

$R_8$, $R_5$ and $R_6$ together, in pairs, may form, with the nitrogen atom to which they are attached, a saturated 4-, 5-, 6- or 7-membered carbon-based ring optionally comprising at least one hetero atom, wherein the ring may possibly be substituted with a radical chosen from a hydroxyl radical, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, carbamoyl radicals, carboxyl radicals, ($C_1$–$C_6$)alkylcarbonyl radicals, amino radicals, and amino radicals mono- or disubstituted with at least one radical chosen from ($C_1$–$C_6$) alkyl, ($C_1$–$C_6$)alkylcarbonyl, carbamoyl and ($C_1$–$C_6$) alkylsulphonyl radicals;

$R_7$ may be chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is mono- or disubstituted with at least one radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ carboxyalkyl radicals; $C_1$–$C_6$ carbamoylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$)alkylcarboxy($C_1$–$C_6$)alkyl radicals; ($C_1$–$C_6$)alkylsulphinyl ($C_1$–$C_6$)alkyl radicals; ($C_1$–$C_6$)alkylsulphonyl($C_1$–$C_6$) alkyl radicals; ($C_1$–$C_6$)alkylcarbonyl($C_1$–$C_6$)alkyl radicals; N—($C_1$–$C_6$)alkylcarbamoyl($C_1$–$C_6$)alkyl radicals; and N—($C_1$–$C_6$)alkylsulphonamido($C_1$–$C_6$)alkyl radicals;

x is equal to 0 or 1, provided that
  when x=0, then the linker arm D is attached to the nitrogen atom bearing the radicals $R_5$, $R_6$ and $R_8$,
  when x=1, then two of the radicals $R_5$, $R_6$ and $R_8$ form, together with the nitrogen atom to which they are attached, a 4-, 5-, 6- or 7-membered saturated ring and the linker arm D is linked to a carbon atom of the saturated ring;

Y is a counterion.

According to this aspect of the present disclosure, x may be, for example, equal to 0, and $R_5$, $R_6$ and $R_8$, which may be identical or different, may each be chosen from $C_1$–$C_6$ alkyl radicals, $C_1$–$C_4$ monohydroxyalkyl radicals, $C_2$–$C_4$ polyhydroxyalkyl radicals, ($C_1$–$C_6$)alkoxy($C_1$–$C_4$)alkyl radicals, $C_1$–$C_6$ carbamoylalkyl radicals, and tri($C_1$–$C_6$)- alkylsilane($C_1$–$C_6$)alkyl radicals, or $R_8$ and $R_5$ together may form a ring chosen from azetidine, pyrrolidine, piperidine, piperazine and morpholine, wherein $R_6$ may be chosen from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals, aminoalkyl radicals mono- or disubstituted with at least one radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ carbamoylalkyl radicals; tri($C_1$–$C_6$)alkylsilane($C_1$–$C_6$)alkyl radicals; ($C_1$–$C_6$)alkylcarboxy($C_1$–$C_6$)alkyl radicals; ($C_1$–$C_6$)alkylcarbonyl($C_1$–$C_6$)alkyl radicals; and N—($C_1$–$C_6$)alkylcarbamoyl($C_1$–$C_6$)alkyl radicals.

According to still another aspect, x is equal to 1, and $R_7$ may be chosen from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine is mono- or disubstituted with at least one radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ carbamylalkyl radicals; tri($C_1$–$C_6$)-alkylsilane($C_1$–$C_6$)alkyl radicals; ($C_1$–$C_6$)alkylcarboxy($C_1$–$C_6$)alkyl radicals; ($C_1$–$C_6$)alkylcarbonyl($C_1$–$C_6$)alkyl radicals; and N—($C_1$–$C_6$)alkylcarbamyl($C_1$–$C_6$)alkyl radicals; $R_8$ and $R_5$ together form a ring chosen from azetidine, pyrrolidine, piperidine, piperazine and morpholine rings, wherein $R_6$ may be chosen from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine is mono- or disubstituted with at least one radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ carbamoylalkyl radicals; tri($C_1$–$C_6$)alkylsilane($C_1$–$C_6$)alkyl radicals; ($C_1$–$C_6$)alkylcarboxy($C_1$–$C_6$)alkyl radicals; ($C_1$–$C_6$)alkylcarbonyl($C_1$–$C_6$)alkyl radicals; and N—($C_1$–$C_6$)alkylcarbamoyl($C_1$–$C_6$)alkyl radicals.

By way of a non-limiting example according to this aspect of the disclosure, $R_2$ may comprise a trialkylammoniumalkyl radical, wherein the alkyl linking $R_2$ to the ring may possibly be substituted with at least one hydroxyl group.

For instance, D may be chosen from a covalent bond and an alkylene chain that may be substituted and that may comprise a carbonyl group.

According to yet another aspect of the present disclosure, $R_2$ comprises an onium radical Z corresponding to formula (III):

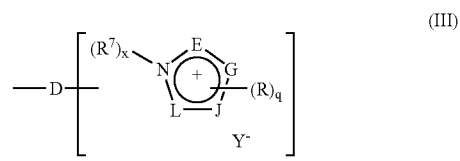

wherein
  D is a linker arm chosen from a covalent bond and from linear and branched $C_1$–$C_{14}$ alkylene chains, which may comprise at least one hetero atom chosen from oxygen, sulphur and nitrogen, and which may be substituted with at least one radical chosen from hydroxyl and amino radicals, and which further may comprise at least one carbonyl radical;
  the ring members E, G, J and L, which may be identical or different, may be chosen from carbon, oxygen, sulphur and nitrogen atoms to form a ring chosen from pyrrole, pyrazole, imidazole, triazole, oxazole, isoxazole, thiazole and isothiazole rings,
  q is an integer ranging from 1 to 4;
  R, which may be identical or different, may be chosen from a hydrogen atom, halogen atoms, hydroxyl radicals, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, carbamoyl radicals, carboxyl radicals, $C_1$–$C_6$ alkylcarbonyl radicals, amino radicals, amino radicals mono- and disubstituted with at least one radical chosen from ($C_1$–$C_6$)alkyl, ($C_1$–$C_6$)alkylcarbonyl, carbamoyl and ($C_1$–$C_6$)alkylsulphonyl radicals, $C_1$–$C_6$ monohydroxyalkyl radicals $C_2$–$C_6$ polyhydroxyalkyl radicals, and quaternary ammonium radicals;
  $R_7$ may be chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals, $C_1$–$C_6$ aminoalkyl radicals wherein the amine is substituted with a radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ carboxyalkyl radicals; $C_1$–$C_6$ carbamoylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$) alkylcarboxy($C_1$–$C_6$)alkyl radicals; ($C_1$–$C_6$)alkylsulphinyl($C_1$–$C_6$)alkyl radicals; ($C_1$–$C_6$)alkylsulphonyl ($C_1$–$C_6$)alkyl radicals; ($C_1$–$C_6$)alkylcarboxy($C_1$–$C_6$)alkyl radicals; N—($C_1$–$C_6$)alkylcarbamoyl($C_1$–$C_6$)alkyl radicals; N—($C_1$–$C_6$)alkylsulphonamido($C_1$–$C_6$)alkyl radicals; and quaternary ammonium radicals;

x is equal to 0 or 1, with the proviso that
when x=0, the linker arm D is attached to the nitrogen atom,
when x=1, the linker arm D is attached to one of the ring members E, G, J or L, and $Y^-$ is a counterion.

According to this aspect of the disclosure, the ring members E, G, J and L form, for example, a ring chosen from pyrrole, imidazole, pyrazole, oxazole, thiazole and triazole rings. For instance, the ring members E, G, J and L may form an imidazole ring.

When x is equal to 0, D may be, for example, chosen from a covalent bond and an alkylene chain that may be substituted and/or that may comprise a carbonyl function.

According to yet still another aspect of the present disclosure, $R_2$ comprises an onium radical Z corresponding to formula (IV):

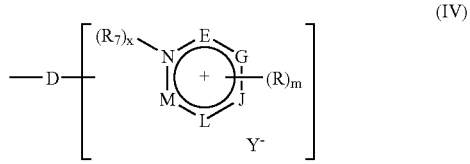

wherein:
D is a linker arm chosen from a covalent bond and from linear and branched $C_1$–$C_{14}$ alkylene chains, which may comprise at least one hetero atom chosen from oxygen, sulphur and nitrogen atoms, and which may be substituted with at least one radical chosen from hydroxyl and amino radicals, and which further may comprise at least one carbonyl radical;
the ring members E, G, J, L and M, which may be identical or different, may be chosen from carbon, oxygen, sulphur and nitrogen atoms, and thus form a ring chosen from pyridine, pyrimidine, pyrazine, triazine and pyridazine rings;
m is an integer ranging from 1 to 5;
R, which may be identical or different, may be chosen from a hydrogen atom, halogen atoms, hydroxyl radicals, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, carbamoyl radicals, carboxyl radicals, $C_1$–$C_6$ alkylcarbonyl radicals, amino radicals, amino radicals substituted with a radical chosen from ($C_1$–$C_6$)alkyl, ($C_1$–$C_6$)alkylcarbonyl, carbamoyl and ($C_1$–$C_6$)alkylsulphonyl radicals, $C_1$–$C_6$ monohydroxyalkyl radicals, $C_2$–$C_6$ polyhydroxyalkyl radicals, and quaternary ammonium radicals;
$R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is mono- and disubstituted with a radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ carboxyalkyl radicals; $C_1$–$C_6$ carbamoylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$)alkylcarboxy($C_1$–$C_6$)alkyl radicals; ($C_1$–$C_6$)alkylsulphinyl($C_1$–$C_6$)alkyl radicals; ($C_1$–$C_6$)alkylsulphonyl ($C_1$–$C_6$)alkyl radicals; ($C_1$–$C_6$)alkylcarboxy($C_1$–$C_6$)alkyl radicals; N—($C_1$–$C_6$)alkylcarbamoyl($C_1$–$C_6$)alkyl radicals; N—($C_1$–$C_6$)alkylsulphonamido($C_1$–$C_6$)alkyl radicals; and quaternary ammonium radicals;

x is equal to 0 or 1, with the proviso that
when x=0, the linker arm D is attached to the nitrogen atom,
when x=1, the linker arm D is attached to one of the ring members E, G, J, L or M, and $Y^-$ is a counterion.

In this aspect, the ring members E, G, J, L and M may form, for example, with the nitrogen of the ring, a ring chosen from pyridine and pyrimidine rings.

For further example, when x is equal to 0, then R may be chosen from a hydrogen atom, hydroxyl radicals, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, carbamoyl radicals, $C_1$–$C_6$ alkylcarbonyl radicals, amino radicals, amino radicals mono- and disubstituted with at least one radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ monohydroxyalkyl radicals and $C_2$–$C_6$ polyhydroxyalkyl radicals.

As yet another example, when x is equal to 1, $R_7$ may be chosen from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine is mono- or disubstituted with at least one radical chosen from ($C_1$–$C_6$)alkyl radicals, ($C_1$–$C_6$)alkylcarbonyl radicals, a carbamoyl radical and ($C_1$–$C_6$)alkylsulphonyl radicals; $C_1$–$C_6$ carbamoylalkyl radicals; tri($C_1$–$C_6$)alkylsilane($C_1$–$C_6$)alkyl radicals; ($C_1$–$C_6$)alkylcarbonyl($C_1$–$C_6$) alkyl radicals; and N—($C_1$–$C_6$)alkylcarbamyl($C_1$–$C_6$)alkyl radicals; R may be chosen from a hydrogen atom, hydroxyl radicals, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, carbamoyl radicals, $C_1$–$C_6$ alkylcarbonyl radicals, amino radicals, amino radicals mono- and disubstituted with at least one radical chosen from ($C_1$–$C_6$)alkyl, ($C_1$–$C_6$)alkylcarbonyl, carbamoyl and ($C_1$–$C_6$)alkylsulphonyl radicals.

For instance, R may be chosen from a hydrogen atom and alkyl radicals that may be substituted, and $R_7$ comprises an alkyl radical that may be substituted.

According to another aspect of the present disclosure, R may be chosen from hydrogen; alkyl radicals; alkyl radicals substituted with at least one hydroxyl; alkyl radicals substituted with at least one amino; carboxyl radicals; and carbamoyl radicals. By way of non-limiting example, mention may be made of when R is chosen from hydrogen and from at least one radical chosen from hydroxyl, methyl, amino, hydroxymethyl, and aminomethyl radicals. In one embodiment, R is hydrogen.

In formula (I) above, for instance, b may be equal to 0, or $R_4$ may be chosen from alkyl radicals; alkyl radicals substituted with at least one hydroxyl; alkyl radicals substituted with at least one amino; carboxyl radicals; and carbamoyl radicals. For example, $R_4$ may be hydrogen.

In formula (I) above, $R_3$ may be, for instance, chosen from hydrogen; hydroxyl radicals; amino radicals; alkyl radicals;

alkyl radicals substituted with at least one hydroxyl; alkyl radicals substituted with at least one amino; carboxyl radicals; and carbamoyl radicals. For example, $R_3$ may be hydrogen.

The carbon substituted with $R_3$ or with $R_4$ may be of (R) and (S) configuration.

The counterions $Y^-$ may be chosen, for example, from a halogen atom, a hydroxide, a hydrogen sulphate, an acetate, a tartrate and a $(C_1-C_6)$alkyl sulphate. For instance, $Y^-$ may be chosen from a methyl sulphate and an ethyl sulphate.

Non-limiting examples of derivatives of formula (I) that may be mentioned include:

| Formula | Nomenclature |
|---|---|
| | 3-{2-[4-(4-Amino-phenyl)[1,4]diazepan-1-yl]-2-oxoethyl}-1-methyl-3H-imidazol-1-ium chloride |
| | 3-{2-[4-(4-Amino-phenyl)[1,4]diazepan-1-yl]ethyl}-1-methyl-3H-imidazol-1-ium chloride |
| | 3-{2-[4-(4-Amino-phenyl)[1,4]diazepan-1-yl]propyl}-trimethylammonium chloride |
| | {2-[4-(4-Amino-phenyl)[1,4]diazepan-1-yl]ethyl}trimethylammonium chloride |
| | 1-{3-[4-(4-Amino-phenyl)[1,4]diazepan-1-yl]propyl}-1-methylpyrrolidinium chloride |
| | {2-[4-(4-Amino-phenyl)[1,4]diazepan-1-yl]ethyl}-(2-hydroxyethyl)dimethylammonium chloride |

-continued

| Formula | Nomenclature |
|---|---|
| 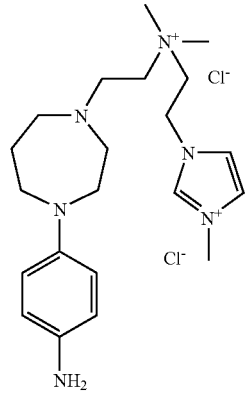 | {3-[4-(4-Amino-phenyl)[1,4]diazepan-1-yl]ethyl}dimethyl(ethyl-2-methyl-3H-imidazol-1-ium chloride)ammonium; chloride |
| 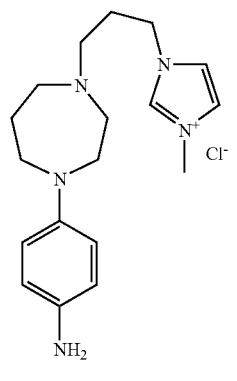 | 3-{2-[4-(4-Amino-phenyl)[1,4]diazepan-1-yl]propyl}-1-methyl-3H-imidazol-1-ium chloride |
| 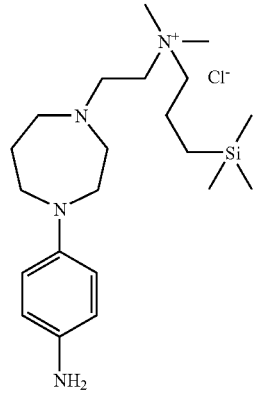 | {2-[4-(4-Amino-phenyl)[1,4]diazepan-1-yl]ethyl}dimethyl-(3-trimethylsilanyl-propyl)ammonium; chloride |
| 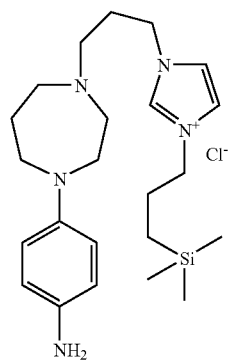 | 3-{2-[4-(4-Amino-phenyl)[1,4]diazepan-1-yl]ethyl}-1-(3-trimethylsilanyl-propyl)-3H-imidazol-1-ium chloride |

-continued

| Formula | Nomenclature |
|---|---|
| 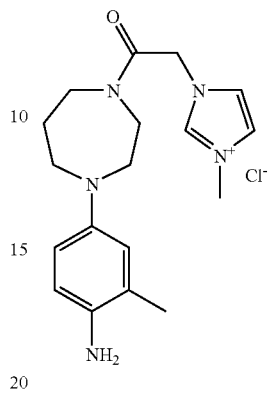 | 3-{2-[4-(4-Amino-3-methylphenyl)[1,4]-diazepan-1-yl]-2-oxoethyl}-1-methyl-3H-imidazol-1-ium chloride |
| 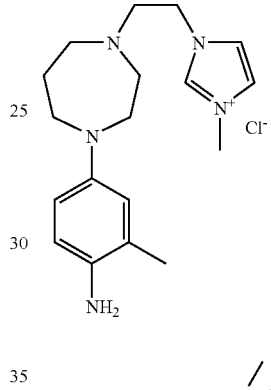 | 3-{2-[4-(4-Amino-3-methylphenyl)[1,4]-diazepan-1-yl]ethyl}-1-methyl-3H-imidazol-1-ium chloride |
| 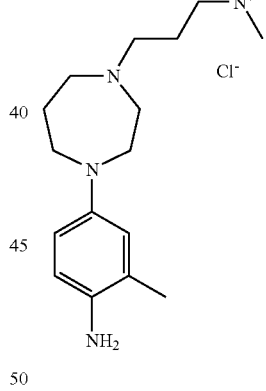 | {3-[4-(4-Amino-3-methylphenyl)[1,4]-diazepan-1-yl]-propyl}trimethylammonium chloride |
| 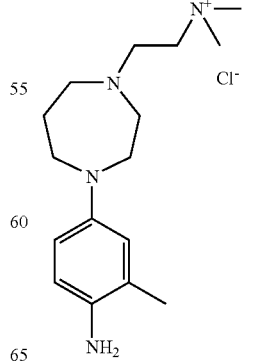 | {2-[4-(4-Amino-3-methylphenyl)[1,4]diazepan-1-yl]ethyl}-trimethylammonium chloride |

-continued

| Formula | Nomenclature |
|---|---|
| | {3-[4-(4-Amino-3-methylphenyl)[1,4]-diazepan-1-yl]-propyl}-1-methyl-3H-imidazol-1-ium chloride |
| | {2-[4-(4-Amino-3-methylphenyl)[1,4]diazepan-1-yl]ethyl}(2-hydroxyethyl)-dimethylammonium chloride |
| | {3-[4-(4-Amino-3-methylphenyl)[1,4]-diazepan-1-yl]ethyl}-dimethyl(ethyl-2-methyl-3H-imidazol-1-ium chloride)ammonium chloride |
| | 1-{3-[4-(4-Amino-3-methylphenyl)[1,4]diazepan-1-yl]propyl}-1-methyl-pyrrolidinium; chloride |

-continued

| Formula | Nomenclature |
|---|---|
| | {2-[4-(4-Amino-3-methylphenyl)[1,4]-diazepan-1-yl]ethyl}-dimethyl(3-trimethylsilanylpropyl)ammonium chloride |
| | 3-{2-[4-(4-Amino-3-methylphenyl)[1,4]diazepan-1-yl]ethyl}-1-(3-trimethylsilanylpropyl)-3H-imidazol-1-ium chloride |
| | {3-[4-(4-Amino-phenyl)[1,4]diazepan-1-yl]-2-hydroxy-propyl}trimethylammonium; chloride |
| | {3-[4-(4-Amino-methylphenyl)[1,4-diazepan-1-yl]-2-hydroxypropyl}trimethylammonium; chloride |

-continued

| Formula | Nomenclature |
|---|---|
| | 3-{2-[4-(4-Amino-phenyl)piperazin-1-yl]-2-oxoethyl}-1-methyl-3H-imidazol-1-ium chloride |
| | {3-[4-(4-Amino-phenyl)piperazin-1-yl]-2-hydroxypropyl} trimethylammonium chloride |
| | 3-{2-[4-(4-Amino-3-methylphenyl)piperazin-1-yl]-2-oxoethyl}-1-methyl-3H-imidazol-1-ium chloride |
| | 3-[4-(4-Amino-3-methylphenyl)piperazin-1-yl]-2-hydroxypropyl}-trimethylammonium chloride |

-continued

| Formula | Nomenclature |
|---|---|
| | 3-{2-[4-(4-Amino-3-phenyl)piperazin-1-yl]ethyl}-1-methyl-3H-imidazol-1-ium chloride |
| | {3-[4-(4-Amino-3-phenyl)piperazin-1-yl]propyl} trimethylammonium chloride |
| | 3-{2-[4-(4-Amino-3-methylphenyl)piperazin-1-yl]ethyl}-1-methyl-3H-imidazol-1-ium chloride |
| | {3-[4-(4-Amino-3-methylphenyl)piperazin-1-yl]-propyl} trimethylammonium chloride |

-continued

| Formula | Nomenclature |
|---|---|
|  | 1-{3-[4-(4-Amino-phenyl)piperazin-1-yl]propyl}-1-methylpyrrolidinium chloride |
|  | 1-{3-[4-(4-Amino-3-phenyl)piperazin-1-yl]propyl}-1-methylpyrrolidinium chloride |

For example, the derivatives of formula (I) may be chosen from:

3-{2-[4-(4-aminophenyl)[1,4]diazepan-1-yl]-2-oxoethyl}-1-methyl-3H-imidazol-1-ium chloride 3-{2-[4-(4-aminophenyl)[1,4]diazepan-1-yl]ethyl}-1-methyl-3H-imidazol-1-ium chloride {3-[4-(4-aminophenyl)[1,4]diazepan-1-yl]propyl}trimethylammonium chloride {2-[4-(4-aminophenyl)[1,4]diazepan-1-yl]ethyl}trimethylammonium chloride 1-{3-[4-(4-aminophenyl)[1,4]diazepan-1-yl]propyl}-1-methylpyrrolidinium chloride {2-[4-(4-aminophenyl)[1,4]diazepan-1-yl]ethyl}(2-hydroxyethyl)dimethylammonium chloride 3-{2-[4-(4-aminophenyl)[1,4]diazepan-1-yl]propyl}-1-methyl-3H-imidazol-1-ium chloride {3-[4-(4-aminophenyl)[1,4]diazepan-1-yl]-2-hydroxypropyl}trimethylammonium chloride 3-{2-[4-(4-aminophenyl)piperazin-1-yl]-2-oxoethyl}-1-methyl-3H-imidazol-1-ium chloride {3-[4-(4-aminophenyl)piperazin-1-yl]-2-hydroxypropyl}trimethylammonium chloride 3-{2-[4-(4-aminophenyl)piperazin-1-yl]ethyl}-1-methyl-3H-imidazol-1-ium chloride {3-[4-(4-aminophenyl)piperazin-1-yl]propyl}trimethylammonium chloride 1-{3-[4-(4-aminophenyl)piperazin-1-yl]propyl}-1-methylpyrrolidinium chloride.

The compounds of formula (I) may be obtained, for example, from the syntheses described in Patent Application FR 2,828,488.

The cationic compounds of formula (I) may be obtained via the following synthetic route:

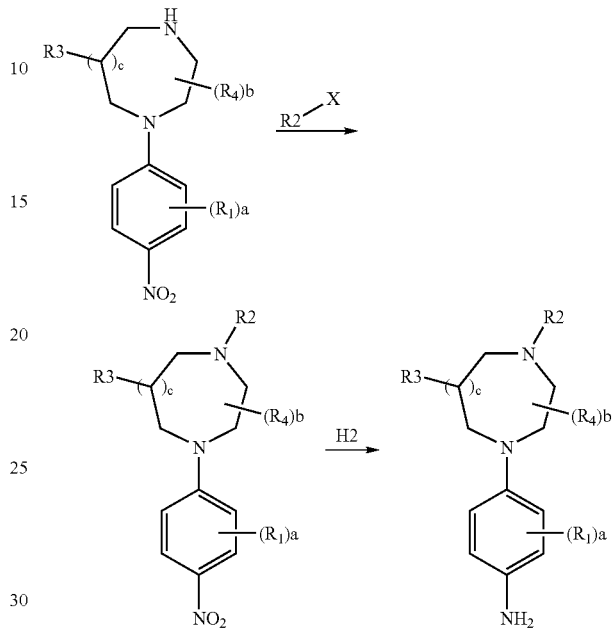

Another aspect of the present invention is also the nitro compounds that are useful in the synthesis of the compounds of formula (I). These nitro compounds correspond to formula (I')

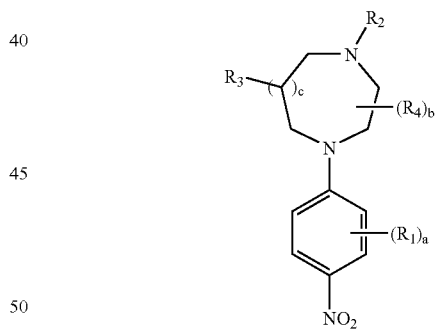

wherein $R_1$, $R_2$, $R_3$, $R_4$, a, b and c are as defined above.

The dye composition of the present disclosure comprises, in a medium that is suitable for dyeing keratin fibers, such as human hair, at least one derivative of formula (I) as defined above as an oxidation base.

The at least one oxidation base of the present disclosure may be present in the composition in an amount, for each oxidation base, if there are more than one, ranging from about 0.001% to about 10% by weight, relative to the total weight of the dye composition, such as from about 0.005% to about 6%.

The dye composition of the present disclosure may comprise at least one coupler conventionally used for dyeing keratin fibers. Among these couplers that may be mentioned, for example, are meta-phenylenediamines, meta-aminophenols, meta-diphenols, naphthalene-based couplers, heterocyclic couplers, and the addition salts thereof.

Non-limiting examples of couplers that may be mentioned include 2-methyl-5-aminophenol, 5-N-(β-hydroxyethyl) amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the acid addition salts thereof.

In the dye composition disclosed herein, the at least one coupler may be present in the dye composition in an amount ranging from about 0.001% to about 10% by weight, relative to the total weight of the dye composition, such as ranging from about 0.005% to about 6%.

The composition of the present disclosure may also optionally comprise at least one additional oxidation base conventionally used in oxidation dyeing, other than theose of formula (I). By way of example, the optional at least one additional oxidation base may be chosen from para-phenylenediamines other than those described above, bis(phenyl)alkylenediamines, para-aminophenols, bis-para-aminophenols, ortho-aminophenols, heterocyclic bases, and the addition salts thereof.

For example, without limitation, among the optional at least one additional para-phenylenediamine mention may be made of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl) pyrrolidine, and the acid addition salts thereof.

Among the para-phenylenediamines mentioned above, for example, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(p-hydroxyethyl)-para-phenylenediamine, 2-chloro-para-phenylenediamine, 2-β-acetylaminoethyloxy-para-phenylenediamine, and the acid addition salts thereof may be used.

Among the bis(phenyl)alkylenediamines that may be used, non-limiting mention may be made, for example, of N,N'-bis(β-hydroxyethyl)-N,N'-bis(4'-aminophenyl)-1,3-diaminopropanol, N,N'-bis(p-hydroxyethyl)-N,N'-bis(4'-aminophenyl)-ethylenediamine, N,N'-bis(4-aminophenyl)tetramethylenediamine, N,N'-bis(β-hydroxyethyl)N,N'-bis(4-aminophenyl)tetramethylenediamine, N,N'-bis(4-methylaminophenyl) tetramethylenediamine, N,N'-bis (ethyl)-N,N'-bis(4'-amino-3'-methylphenyl) ethylenediamine, 1,8-bis(2,5-diaminophenoxy)-3,6-dioxaoctane, and the acid addition salts thereof.

Among the para-aminophenols which may be used, non-limiting mention may be made, for example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the acid addition salts thereof.

Among the ortho-aminophenols which can be used, non-limiting mention may be made, for example, of 2-aminophenol, 2-amino-5-methylphenol, 2-amino-6-methylphenol, 5-acetacarbamoyl-2-aminophenol, and the acid addition salts thereof.

Among the heterocyclic bases that may be used, non-limiting mention may be made, for example, of pyridine derivatives, pyrimidine derivatives and pyrazole derivatives.

Among the pyridine derivatives that may be used, non-limiting mention may be made of the compounds described, for example, in patents GB 1,026,978 and GB 1,153,196, as well as 2,5-diaminopyridine; 2-(4-methoxyphenyl)amino-3-aminopyridine; 2,3-diamino-6-methoxypyridine; 2-(β-methoxyethyl)amino-3-amino-6-methoxypyridine; 3,4-diaminopyridine; and the acid addition salts thereof.

Other pyridine oxidation bases that may be useful in the present dye composition as disclosed herein are the 3-aminopyrazolo[1,5-a]pyridine oxidation bases and the addition salts thereof described, for example, in patent application FR 2,801,308. By way of example, non-limiting mention may be made of pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2,3-aminopyrazolo[1,5-a]pyrid-7-yl)ethanol; (3-aminopyrazolo[1,5-a] pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino] ethanol; 2-[(3-aminopyrazolo[1,5-a]pyrid-7-yl) (2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol and also the addition salts thereof with an acid or with a base.

Among the pyrimidine compounds which may be used, non-limiting mention may be made of the compounds described, for example, in German Patent DE 2,359399, or Japanese Patents JP 88-169,571; JP 05,63,124; EP 0,770,375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine. Among the pyrazolopyrimidine derivatives that may be used, non-limiting mention may be made for instance, of those mentioned in patent application FR-A-2,750,048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5, N7, N7-tetramethylpyrazolo[1,5-a]pyrimidine-3,7-diamine; 3-amino-5-methyl-7-imidazolylpropylaminopyrazolo[1,5-a]pyrimidine; and the acid addition salts thereof and the tautomeric forms thereof, when a tautomeric equilibrium exists.

Among the pyrazole derivatives that may be used, non-limiting mention may be made of the compounds described in patents DE 3,843,892 and DE 4,133,957 and patent applications WO 94/08969, WO 94/08970, FR-A-2,733,749 and DE 195,43,988, such as 4,5-diamino-1-methylpyrazole; 4,5-diamino-1-(β-hydroxyethyl)pyrazole; 3,4-diaminopyrazole; 4,5-diamino-1-(4'-chlorobenzyl)pyrazole; 4,5-diamino-1,3-dimethylpyrazole; 4,5-diamino-3-methyl-1-phenylpyrazole; 4,5-diamino-1-methyl-3-phenylpyrazole; 4-amino-1,3-dimethyl-5-hydrazinopyrazole; 1-benzyl-4,5-diamino-3-methylpyrazole; 4,5-diamino-3-tert-butyl-1-methylpyrazole; 4,5-diamino-1-tert-butyl-3-methylpyrazole; 4,5-diamino-1-(β-hydroxyethyl)-3-methylpyrazole; 4,5-diamino-1-ethyl-3-methylpyrazole; 4,5-diamino-1-ethyl-3-(4'-methoxyphenyl)pyrazole; 4,5-diamino-1-ethyl-3-hydroxymethylpyrazole; 4,5-diamino-3-hydroxymethyl-1-methylpyrazole; 4,5-diamino-3-hydroxymethyl-1-isopropylpyrazole; 4,5-diamino-3-methyl-1-isopropylpyrazole; 4-amino-5-(2'-aminoethyl)amino-1,3-dimethylpyrazole; 3,4,5-triaminopyrazole; 1-methyl-3,4,5-triaminopyrazole; 3,5-diamino-1-methyl-4-methylaminopyrazole; 3,5-diamino-4-(β-hydroxyethyl)amino-1-methylpyrazole; and the acid addition salts thereof.

As defined above, the optional at least one additional oxidation base, when present, is present in an amount, for each additional oxidation base, ranging from about 0.001% to about 10% by weight relative to the total weight of the dye composition, for example, from about 0.005% to about 6%.

The addition salts of the oxidation bases and of the couplers that may be used in the dye compositions disclosed herein may be chosen from, for example, the addition salts with an acid, such as the hydrochlorides, hydrobromides, sulphates, citrates, succinates, tartrates, lactates, tosylates, benzenesulphonates, phosphates and acetates; and the addition salts with a base, such as sodium hydroxide, potassium hydroxide, ammonia, amines and alkanolamines.

The dye composition in accordance with the present disclosure may also comprise at least one direct dye that may be chosen from for example, nitrobenzene dyes, azo direct dyes and methine direct dyes. The direct dyes may be of nonionic, anionic or cationic nature.

A medium suitable for dyeing, also known as the dye support, comprises water or a mixture of water and at least one organic solvent to dissolve the compounds that would not be sufficiently soluble in water. Among the organic solvents that may be used, non-limiting mention may be made, for example, of $C_1$–$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, as well as aromatic alcohols such as benzyl alcohol, phenoxyethanol, and mixtures thereof.

The at least one solvent may be present in the dye composition in an amount, for example, ranging from about 1% to about 40% by weight, relative to the total weight of the dye composition, such as ranging from about 5% to about 30% by weight.

The dye composition in accordance with the present disclosure can also comprise various adjuvants conventionally used in compositions for dyeing the hair, such as anionic, cationic, nonionic, amphoteric, and zwitterionic surfactants and mixtures thereof; anionic, cationic, nonionic, amphoteric, and zwitterionic polymers, and mixtures thereof; inorganic or organic thickeners, for instance, anionic, cationic, nonionic and amphoteric associative polymeric thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

The above adjuvants may be present in the dye composition in an amount for each of them ranging from about 0.01% to about 20% by weight, relative to the total weight of the dye composition.

Needless to say, a person skilled in the art will take care to select any of the optional additional compounds such that the advantageous properties intrinsically associated with the oxidation dye composition in accordance with the present disclosure are not, or are not substantially, adversely affected by the addition envisaged.

The pH of the dye composition in accordance with the present disclosure may range from about 3 to about 12, such as from about 5 to about 11. It may be adjusted to the desired value using acidifying or basifying agents usually used in the dyeing of keratin fibers, or alternatively using standard buffer systems.

Among the acidifying agents that may be used, non-limiting mention may be made, for example, of inorganic and organic acids such as hydrochloric acid, orthophosphoric acid, sulphuric acid, carboxylic acids such as acetic acid, tartaric acid, citric acid, lactic acid, and sulphonic acids.

Among the basifying agents that may be used, non-limiting mention may be made, for example, of aqueous ammonia, alkaline carbonates, alkanolamines such as mono-, di- and triethanolamine and derivatives thereof, sodium hydroxide, potassium hydroxide and the compounds of formula (V):

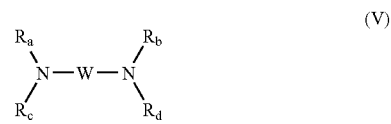

wherein W is a propylene residue that may be unsubstituted, or substituted with a hydroxyl group or a $C_1$–$C_4$ alkyl radical; $R_a$, $R_b$, $R_c$ and $R_d$, which may be identical or different, are chosen from a hydrogen atom, $C_1$–$C_4$ alkyl radicals and $C_1$–$C_4$ hydroxyalkyl radicals.

The dye composition according to the present disclosure may be in various forms, such as liquids, creams and gels, or in any other form that is suitable for dyeing keratin fibers, such as human hair.

The process of the present disclosure is a process wherein the dye composition as described above is applied to the fibers, and the color is developed using an oxidizing agent. The color may be developed at acidic, neutral or alkaline pH and the oxidizing agent may be added to the composition as disclosed herein just at the time of use, or it may be used starting with an oxidizing composition comprising it, which is applied simultaneously or sequentially to the composition of the invention.

According to one aspect, the dye composition according to the present disclosure is mixed, for example, at the time of use, with a composition comprising, in a medium that is suitable for dyeing, at least one oxidizing agent, this oxidizing agent being present in an amount that is sufficient to develop a coloration. The mixture obtained is then applied to keratin fibers. After an action time of 3 to 50 minutes approximately, such as 5 to 30 minutes approximately, the keratin fibers are rinsed, washed with shampoo, rinsed again and then dried.

The oxidizing agents conventionally used for the oxidation dyeing of keratin fibers include, for example, hydrogen peroxide, urea peroxide, alkali metal bromates, persalts such as perborates and persulphates, peracids and oxidase enzymes, among which, non-limiting mention may be made of peroxidases, 2-electron oxidoreductases such as uricases, and 4-electron oxygenases, for instance laccases. For example, the oxidizing agent may be hydrogen peroxide.

The oxidizing composition may also comprise various adjuvants conventionally used in compositions for dyeing the hair and as defined above.

The pH of the oxidizing composition comprising the oxidizing agent is such that, after mixing with the dye composition, the pH of the resulting composition applied to the keratin fibers ranges for example, from about 3 to about 12, for instance from about 5 to about 11. The pH may be adjusted to the desired value by means of acidifying or basifying agents usually used in the dyeing of keratin fibers and as defined above.

The ready-to-use composition that is finally applied to the keratin fibers may be in various forms, such as in the form of liquids, creams, gels, or any other form that is suitable for dyeing keratin fibers, such as human hair.

Another aspect of the present disclosure is a multi-compartment dyeing device or "kit," in which at least one first compartment contains the dye composition as disclosed herein, and at least one second compartment contains an oxidizing composition. This device may be equipped with a means for applying the desired mixture to the hair, such as the devices described in patent FR-2,586,913 in the name of L'Oreal.

Using this device, it is possible to dye keratin fibers using a process that includes mixing a dye composition comprising at least one oxidation base of formula (I) with an oxidizing agent, and applying the mixture obtained to the keratin fibers for a time that is sufficient to develop the desired coloration.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result.

EXAMPLES

Example 1

Preparation of 3-{2-[4-(4-aminophenyl)[1,4]diazepan-1-yl]-2-oxoethyl}-1-methyl-3H-imidazol-1-ium chloride dihydrochloride (4)

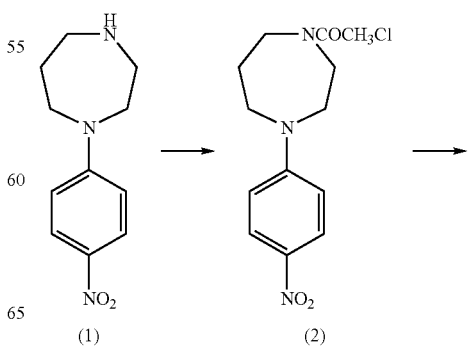

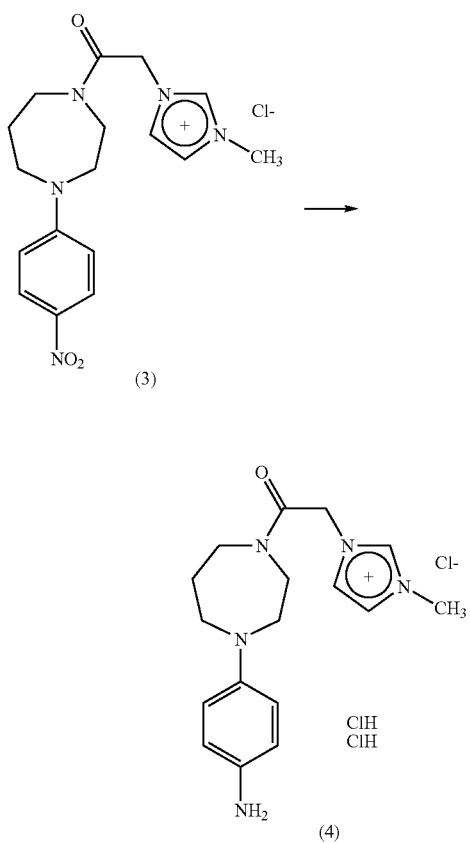

(3)

(4)

1st Step: Synthesis of 2-chloro-1-[4-(4-nitrophenyl)
[1,4]diazepan-1-yl]ethanone (2)

22.1 g (0.1 mol) of 1-(4-nitrophenyl)[1,4]diazepane, 8.3 g (0.06 mol) of potassium carbonate and 120 ml of dimethylformamide were mixed together in a reactor. 8.3 ml (0.11 mol) of chloroacetyl chloride were added to this stirred suspension, while maintaining the temperature between 15 and 25° C. After stirring for about ten hours at room temperature, 400 g of slightly hydrochloric ice-cold water were added to the mixture: a yellow gum crystallized. After filtering off by suction, washing with water and drying under vacuum over phosphorus pentoxide, 22.4 g of yellow crystals were obtained (yield=75%).

$^1$H NMR (400 MHz, DMSO D6): 1.83 (m), 1.9 (m), 3.37 (t), 3.47 (t), 3.67 (m), 3.85 (t), 4.28 (s), 4.36 (s), 6.9 (m), 8.04 (m).

2nd Step: Synthesis of 3-methyl-1-{2-[4-(4-nitrophenyl)[1,4]diazepan-1-yl]-2-oxoethyl}-3H-imidazol-1-ium chloride (3)

A mixture of 19.95 g (0.067 mol) of 2-chloro-1-[4-(4-nitrophenyl)[1,4]diazepan-1-yl]ethanone obtained above in the preceding step and 11.5 g (0.14 mol) of 1-methyl-1H-imidazole in 40 ml of isobutanol were refluxed for 1 hour 30 minutes with stirring. After crystallization under cold conditions, a precipitate of yellow crystals was obtained. This precipitate was then washed with isobutanol and then with ethyl ether and dried at 40° C. under vacuum and over phosphorus pentoxide.

After recrystallization from 65 ml of refluxing ethanol, 14.0 g of a yellow crystalline compound were obtained (yield=55%).

$^1$H NMR (400 MHz, DMSO D6): 1.85–2 (2m, 2H), 3.37–3.5 (2m, 2H), 3.72–3.89–3.95 (2 m+2s, 9H), 5.385–5.389 (2s, 2H), 6.93 (2m, 2H), 7.61 (2dd, 1H), 7.68 (2dd, 1H), 8.05 (2m, 2H), 9.08–9.1 (2dd, 1H).

3rd Step: Synthesis of 3-[2-[4-(4-aminophenyl)[1,4]diazepan-1-yl]-2-oxymethyl]-1-methyl-3H-imidazol-1-ium chloride dihydrochloride (4)

13.1 g (0.0345 mol) of 3-methyl-1-{2-[4-(4-nitrophenyl)[1,4]diazepan-1-yl]-2-oxoethyl)-3H-imidazol-1-ium chloride, obtained in the preceding step, 3 g of palladium-on-charcoal (containing 50% water), 400 ml of 960 ethanol and 150 ml of water were placed in a one-liter hydrogenator.

The reduction was performed over two hours under a hydrogen pressure of about five bar and at a temperature of 70° C. After filtering off the catalyst under nitrogen, aqueous hydrochloric acid was poured onto the mixture.

After evaporating the filtrate under reduced pressure, recrystallizing the mixture from refluxing ethanol, hydrochloric acid, and water, and drying at 40° C. under vacuum and over potassium hydroxide, 15.9 g (yield=75%) of white crystals were obtained.

The elemental analysis calculated for $C_{17}H_{26}N_5OCl_3$+$H_2O$+$CH_3CH_2OH$ was:

| | C % | H % | N % | O % | Cl % |
|---|---|---|---|---|---|
| Calculated: | 48.87 | 7.04 | 14.38 | 9.86 | 21.85 |
| Found: | 46.82 | 6.89 | 14.42 | 9.41 | 22.39 |

The $^{13}$C NMR and $^1$H NMR spectra were in accordance with the expected structure.

$^1$H NMR (400 MHz, $D_2O$): 2.21–2.47 (2m, 2H), 3.78–3.89 (m, 4H), 3.97–4.09 (m+s, 7H), 5.27–5.42 (2H), 7.33–7.72 (m, 6H), 8.71–8.8 (2s, 1H). $^{13}$C NMR ($D_2O$): 23.25; 24.32; 35.89; 41.77; 43.44; 44.96; 45.42; 50.17; 53.98; 55.94; 54.59; 56.5; 118.25; 120.69; 123.1; 123.27; 123.55; 123.68; 124.9; 124.99; 125.53; 128.71; 137; 143.6; 144.8; 166.16; 166.74.

The mass spectrum showed that the expected cation, $C_{17}H_{24}N_5O^+$, is mainly detected at m/z=314 in ES+.

Example 2

2-hydroxy-N,N,N-trimethyl-3-[4-(4-aminophenyl)-1,4-diazepan-1-yl]propan-1-aminium acetate (3)

Synthesis of 2-hydroxy-N,N,N-trimethyl-3-[4-(4-nitrophenyl)-1,4-diazepan-1-yl]propan-1-aminium acetate (2)

1.1 g of 1-(4-nitrophenyl)-1,4-diazepane (0.005 mol), 3 ml of DMF and 0.76 g (0.00448 mol) of glycidyltrimethylammonium were placed in a three-necked flask. The mixture was heated at 105° C. for 20 hours. The reaction mixture was then poured into 50 ml of ethyl acetate. After triturating the gum and removing the ethyl acetate, the product was taken up in water and extracted with butanol, and the aqueous phase was concentrated. A sample was purified by preparative HPLC.

$^1$H NMR (DMSO $d_6$, 200 MHz, ppm) was in accordance with the expected product: 8.03 (d, 2H); 6.84 (d, 2H); 4.25 (m, 1H); 3.23–3.67 (m, 8H); 3.095 (s, 9H); 2.823 (m, 2H); 2.5–2.615 (m, 2H); 1.83 (m, 2H); 1.69 (s, 3H). Mass ESI$^+$: m/z=337[M$^+$].

Synthesis of 2-hydroxy-N,N,N-trimethyl-3-[4-(4-aminophenyl)-1,4-diazepan-1-yl]propan-1-aminium acetate (3)

After reduction with zinc/acetic acid, 2-hydroxy-N,N,N-trimethyl-3-[4-(4-aminophenyl)-1,4-diazepan-1-yl]propan-1-aminium acetate was obtained.

Mass ESI$^+$: m/z=307[M$^+$].

EXAMPLES OF DYEING

Examples 1 to 7

Dyeing in alkaline medium using 3-{2-[4-(4-aminophenyl) [1,4]diazepan-1-yl]-2-oxoethyl}-1-methyl-3H-imidazol-1-ium Chloride Dihydrochloride The dye compositions below were prepared:

| Examples | 1 | 2 | 3 | 4 | 5 | 6 | 7 |
|---|---|---|---|---|---|---|---|
| 3-{2-[4-(4-Aminophenyl) [1,4]diazepan-1-yl]-2-oxoethyl}-1-methyl-3H-imidazol-1-ium chloride dihydrochloride (base) | 10$^{-3}$ mol | 10$^{-3}$ mol | 10$^{-3}$ mol | — | — | — | — |
| 2-Hydroxy-N,N,N-trimethyl-3-[4-(4-amino phenyl)-1,4-diazepan-1-yl]propan-1-aminium acetate (base) | — | — | — | 10$^{-3}$ mol | 10$^{-3}$ mol | 10$^{-3}$ mol | 10$^{-3}$ mol |
| 2-(2,4-Diaminophenoxy) ethanol dihydrochloride (coupler) | 10$^{-3}$ mol | — | — | 10$^{-3}$ mol | — | — | — |
| 3-Amino-2-chloro-6-methylphenol hydrochloride (coupler) | — | 10$^{-3}$ mol | — | — | 10$^{-3}$ mol | — | — |
| 3,6-Dimethyl-1H-pyrazolo [5,1-c]-[1,2,4]triazole (coupler) | — | — | 10$^{-3}$ mol | — | — | 10$^{-3}$ mol | — |
| 2-Methyl-5-aminophenol (coupler) | — | — | — | — | — | — | 10$^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

-continued

| Examples | 1 | 2 | 3 | 4 | 5 | 6 | 7 |
|---|---|---|---|---|---|---|---|
| (*) Dye support (1) pH 9.5 | | | | | | | |
| 96° ethyl alcohol | 20.8 g | | | | | | |
| Sodium metabisulphite as an aqueous 35% solution | 0.23 g A.M. | | | | | | |
| Pentasodium salt of diethylene triamine pentacetic acid as an aqueous 40% solution | 0.48 g A.M. | | | | | | |
| $C_8$–$C_{10}$ alkyl polyglucoside as an aqueous 60% solution | 3.6 g A.M. | | | | | | |
| Benzyl alcohol | 2.0 g | | | | | | |
| Polyethylene glycol containing 8 ethylene oxide units | 3.0 g | | | | | | |
| $NH_4Cl$ | 4.32 g | | | | | | |
| Aqueous ammonia containing 20% $NH_3$ | 2.94 g | | | | | | |

At the time of use, each composition was mixed with an equal weight of 20-volumes aqueous hydrogen peroxide solution (6% by weight). A final pH of 9.5 was obtained.

Each mixture obtained was applied to locks of grey hair containing 90% white hairs. After a leave-in time of 30 minutes, the locks were rinsed, washed with a standard shampoo, rinsed again and then dried.

The following dyeing results were obtained.

| Examples | 1 | 2 | 3 | 4 | 5 | 6 | 7 |
|---|---|---|---|---|---|---|---|
| Shade observed | Blue | Blue-violet | Chromatic red-violet | Blue | Blue-violet | Chromatic red-violet | Grey-violet |

Examples 8 to 16

Dyeing in acidic medium using 3-(2-[4-(4-aminophenyl)[1,4]diazepan-1-yl]-2-oxoethyl}-1-methyl-3H-imidazol-1-ium chloride dihydrochloride The following dye compositions were prepared:

| Examples | 8 | 9 | 10 | 11 |
|---|---|---|---|---|
| 3-{2-[4-(4-Amino-phenyl)[1,4]diazepan-1-yl]-2-oxoethyl}-1-methyl-3H-imidazol-1-ium chloride; dihydrochloride (base) | $10^{-3}$ mol | $10^{-3}$ mol | $10^{-3}$ mol | $10^{-3}$ mol |
| 2-(2,4-Diaminophenoxy)-ethanol dihydrochloride (coupler) | $10^{-3}$ mol | | | |
| 3-Amino-2-chloro-6-methyphenol hydrochloride (coupler) | | $10^{-3}$ mol | | |
| 2-Methyl-5-aminophenol (coupler) | | | $10^{-3}$ mol | |
| 2-Aminopyridin-3-ol (coupler) | | | | $10^{-3}$ mol |
| Dye support (2) | (*) | (*) | (*) | (*) |
| Demineralized water qs | 100 g | 100 g | 100 g | 100 g |

| Examples | 12 | 13 | 14 | 15 | 16 |
|---|---|---|---|---|---|
| 2-Hydroxy-N,N,N-trimethyl-3-[4-(4-aminophenyl)-1,4-diazepan-1-yl]propan-1-aminium acetate (base) | $10^{-3}$ mol | $10^{-3}$ mol | $10^{-3}$ mol | $10^{-3}$ mol | $10^{-3}$ mol |

| -continued | | | | | |
|---|---|---|---|---|---|
| 2-(2,4-Diamino-phenoxy)ethanol dihydrochloride (coupler) | $10^{-3}$ mol | — | — | — | — |
| 3-Amino-2-chloro-6-methyphenol hydrochloride (coupler) | — | $10^{-3}$ mol | — | — | — |
| 2-Methyl-5-aminophenol (coupler) | — | — | $10^{-3}$ mol | — | — |
| 2-Aminopyridin-3-ol (coupler) | — | — | — | $10^{-3}$ mol | — |
| 6-Hydroxy-1-H-indole (coupler) | — | — | — | — | $10^{-3}$ mol |
| Dye support (2) | (*) | (*) | (*) | (*) | (*) |
| Demineralized water qs | 100 g | 100 g | 100 g | 100 g | 100 g |

(*) Dye support (2) pH 7

| | |
|---|---|
| 96° ethyl alcohol | 20.8 g |
| Sodium metabisulphite as an aqueous 35% solution | 0.23 g A.M. |
| Pentasodium salt of diethylene triamine pentacetic acid as an aqueous 40% solution | 0.48 g A.M. |
| $C_8$–$C_{10}$ alkyl polyglucoside as an aqueous 60% solution | 3.6 g A.M. |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair containing 90% white hairs. After a leave-in time of 30 minutes, the locks were rinsed, washed with a standard shampoo, rinsed again and then dried.

The following dyeing results were obtained.

| Examples | 8 | 9 | 10 | 11 | 12 | 13 | 14 | 15 | 16 |
|---|---|---|---|---|---|---|---|---|---|
| Shade observed | Violet-blue | Blue-violet | Violet | Grey-violet | Blue | Violet | Brown-violet | Brown-grey | Brown-grey |

What is claimed is:

1. A compound of formula (I), and the addition salts thereof

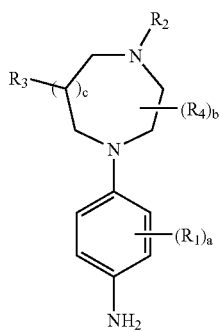

(I)

wherein:
a ranges from 0 to 4, it being understood that when a is greater than or equal to 2, then the radicals $R_1$ may be identical or different,
b ranges from 0 to 4, it being understood that when b is greater than or equal to 2, then the radicals $R_4$ may be identical or different,
c is equal to 0 or 1, $R_1$ is chosen from a halogen atom; $C_1$–$C_8$ aliphatic and alicyclic, saturated and unsaturated hydrocarbon-based chains, wherein at least one carbon atom is optionally replaced with at least one entity chosen from oxygen, nitrogen, silicon, and sulphur atoms and an $SO_2$ group; and an onium radical Z; with the proviso that the radical $R_1$ does not comprise a peroxide bond or diazo, nitro or nitroso radicals, $R_2$ comprises an onium radical Z, wherein an onium radical is a nitrogen-based quaternary radical, $R_3$ is chosen from
an alkyl radical;
an alkenyl radical;
an alkynyl radical;
a hydroxyl radical;
a hydroxyalkyl radical;
an alkoxy radical;
an alkoxyalkyl radical;
an alkylcarbonyl radical;
a hydroxyalkoxyalkyl radical;
an amino radical;

a monoalkylamino radical;
a dialkylamino radical;
an aminoalkyl radical;
an aminoalkyl radical wherein the amine is monosubstituted or disubstituted with at least one radical chosen from alkyl, acetyl and hydroxyalkyl radicals;
a hydroxyl radical;
a aminoalkyl radical;
a carboxyl radical;
a carboxyalkyl radical;
a carbamoyl radical;
a carbamoylalkyl radical;
an alkoxycarbonyl radical;
a monoalkylaminocarbonyl radical;
a dialkylaminocarbonyl radical;
a monoalkylaminocarbonylalkyl radical; and
a dialkylaminocarbonylalkyl radical;
$R_4$ is chosen from
an alkyl radical;
an alkenyl radical;
an alkynyl radical;
a hydroxyalkyl radical;
an alkoxyalkyl radical;
an alkylcarbonyl radical;
a hydroxyalkoxyalkyl radical;
an aminoalkyl radical;
an aminoalkyl radical wherein the amine is monosubstituted or disubstituted with at least one radical chosen from alkyl, acetyl and hydroxyalkyl radicals;
a hydroxyl radical;
a aminoalkyl radical;
a carboxyl radical;
a carboxyalkyl radical;
a carbamoyl radical;
a carbamoylalkyl radical;
an alkoxycarbonyl radical;
a monoalkylaminocarbonyl radical;
a dialkylaminocarbonyl radical;
a monoalkylaminocarbonylalkyl radical; and
a dialkylaminocarbonylalkyl radical.

2. The compound according to claim 1, wherein $R_1$ is chosen from $C_1$–$C_4$ alkyl radicals, $C_1$–$C_4$ alkoxyalkyl radicals, $C_1$–$C_4$ hydroxyalkyl radicals, $C_1$–$C_4$ aminoalkyl radicals, $C_1$–$C_4$ alkoxy radicals, $C_1$–$C_4$ hydroxyalkoxy radicals, and $C_1$–$C_4$ carboxyalkyl radicals.

3. The compound according to claim 2, wherein $R_1$ is chosen from methyl, hydroxymethyl, 2-hydroxyethyl, 1,2-dihydroxyethyl, methoxy, isopropyloxy and 2-hydroxyethoxy radicals.

4. The compound according to claim 1, wherein a is equal to 0 or 1.

5. The compound according to claim 1, wherein $R_2$ is an onium radical Z of formula (II)

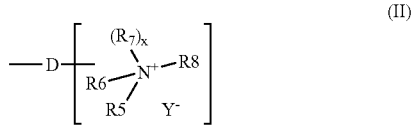

(II)

wherein:
D is a linker arm chosen from a covalent bond and from linear and branched $C_1$–$C_{14}$ alkylene chains, which may comprise at least one hetero atom chosen from oxygen, sulphur and nitrogen, and which may be substituted with at least one radical chosen from hydroxyl and amino radicals, and which may further optionally comprise at least one carbonyl radical;

$R_8$, $R_5$ and $R_6$, which may be identical or different, are each separately chosen from $C_1$–$C_{15}$ alkyl radicals; $C_1$–$C_6$ monohydroxyalkyl radicals; $C_2$–$C_6$ polyhydroxyalkyl radicals; $(C_1$–$C_6)$alkoxy$(C_1$–$C_6)$alkyl radicals; aryl radicals; benzyl radicals; $C_1$–$C_6$ carbamoylalkyl radicals; tri$(C_1$–$C_6)$alkylsilane$(C_1$–$C_6)$alkyl radicals; $C_1$–$C_6$ aminoalkyl radicals; $C_1$–$C_6$ aminoalkyl radicals wherein the amine is mono- or disubstituted with at least one radical chosen from $C_1$–$C_4$ alkyl, $(C_1$–$C_6)$alkylcarbonyl, carbamoyl and $(C_1$–$C_6)$alkylsulphonyl radicals; and quaternary ammonium radicals;

$R_8$, $R_5$ and $R_6$ together, in pairs, form, with the nitrogen atom to which they are attached, a saturated 4-, 5-, 6- or 7-membered carbon-based ring optionally comprising at least one hetero atom, wherein the ring may optionally be substituted with a radical chosen from hydroxyl radicals, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri$(C_1$–$C_6)$alkylsilane $(C_1$–$C_6)$alkyl radicals, carbamoyl radicals, carboxyl radicals, $(C_1$–$C_6)$alkylcarbonyl radicals, amino radicals, and amino radicals mono- and disubstituted with at least one radical chosen from $(C_1$–$C_6)$alkyl, $(C_1$–$C_6)$ alkylcarbonyl, carbamoyl and $(C_1$–$C_6)$alkylsulphonyl radicals;

$R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is mono- or disubstituted with at least one radical chosen from $(C_1$–$C_6)$alkyl, $(C_1$–$C_6)$alkylcarbonyl, carbamoyl and $(C_1$–$C_6)$alkylsulphonyl radicals; $C_1$–$C_6$ carboxyalkyl radicals; $C_1$–$C_6$ carbamoylalkyl radicals; $C_1$–$C_6$ trifluoroalkyl radicals; tri$(C_1$–$C_6)$alkylsilane$(C_1$–$C_6)$ alkyl radicals; $C_1$–$C_6$ sulphonamidoalkyl radicals; $(C_1$–$C_6)$alkylcarboxy$(C_1$–$C_6)$alkyl radicals; $(C_1$–$C_6)$ alkylsulphinyl$(C_1$–$C_6)$alkyl radicals; $(C_1$–$C_6)$alkylsulphonyl$(C_1$–$C_6)$alkyl radicals; $(C_1$–$C_6)$alkylcarbonyl $(C_1$–$C_6)$alkyl radicals; N—$(C_1$–$C_6)$alkylcarbamoyl $(C_1$–$C_6)$alkyl radicals; and N—$(C_1$–$C_6)$ alkylsulphonamido$(C_1$–$C_6)$alkyl radicals;

x is equal to 0 or 1, with the proviso that
when x=0, then the linker arm D is attached to the nitrogen atom bearing the radicals $R_5$, $R_6$ and $R_8$,
when x=1, then two of the radicals $R_5$, $R_6$ and $R_8$ form, together with the nitrogen atom to which they are attached, a 4-, 5-, 6- or 7-membered saturated ring and the linker arm D is linked to a carbon atom of the saturated ring;

$Y^-$ is a counterion.

6. The compound according to claim 5, wherein:
x is equal to 0, and
$R_5$, $R_6$ and $R_8$ are each separately chosen from $C_1$–$C_6$ alkyl radicals, $C_1$–$C_4$ monohydroxyalkyl radicals, $C_2$–$C_4$ polyhydroxyalkyl radicals, $(C_1$–$C_6)$alkoxy $(C_1$–$C_4)$alkyl radicals, $C_1$–$C_6$ carbamoyl alkyl radicals, and tri$(C_1$–$C_6)$alkylsilane$(C_1$–$C_6)$alkyl radicals, or wherein $R_8$ and $R_5$ together form a ring chosen from azetidine, pyrrolidine, piperidine, piperazine and morpholine rings, and wherein $R_6$ is chosen from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; aminoalkyl radicals mono- and disubstituted with at least one radical chosen from $(C_1$–$C_6)$alkyl, ($C_1$–$C_6$)alkylcarbonyl, carbamoyl and ($C_1$–$C_6$)alkylsulphonyl radicals; $C_1$–$C_6$ carbamoylalkyl radicals; tri($C_1$–$C_6$)alkylsilane($C_1$–$C_6$)alkyl radicals; ($C_1$–$C_6$)alkylcarboxy($C_1$–$C_6$)alkyl radicals; ($C_1$–$C_6$)alkylcarbonyl($C_1$–$C_6$)alkyl radicals; and N—($C_1$–$C_6$)-alkylcarbamoyl($C_1$–$C_6$)alkyl radicals.

7. The compound according to claim 5, wherein
x is equal to 1;
$R_7$ is chosen from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine is mono- or disubstituted with at least one radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ carbamylalkyl radicals; tri($C_1$–$C_6$)alkylsilane($C_1$–$C_6$)alkyl radicals; ($C_1$–$C_6$)alkylcarboxy($C_1$–$C_6$)alkyl radicals; ($C_1$–$C_6$)alkylcarbonyl($C_1$–$C_6$)alkyl radicals; and N—($C_1$–$C_6$)alkylcarbamyl($C_1$–$C_6$)alkyl radicals;
$R_8$ and $R_5$ together form a ring chosen from azetidine, pyrrolidine, piperidine, piperazine and morpholine rings; and
$R_6$ is chosen from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine is mono- or disubstituted with at least one radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ carbamoylalkyl radicals; tri($C_1$–$C_6$)alkylsilane($C_1$–$C_6$)alkyl radicals; ($C_1$–$C_6$)alkylcarboxy($C_1$–$C_6$)alkyl radicals; ($C_1$–$C_6$)alkylcarbonyl($C_1$–$C_6$)alkyl radicals; and N—($C_1$–$C_6$)alkylcarbamoyl($C_1$–$C_6$)alkyl radicals.

8. The compound according to claim 5, wherein $R_2$ comprises a trialkylammonium alkyl radical, and further wherein the alkyl linking $R_2$ to the ring is optionally substituted with at least one hydroxyl group.

9. The compound according to claim 5, wherein D is chosen from a covalent bond and an alkylene chain that may optionally be substituted and/or may comprise a carbonyl group.

10. The compound according to claim 1, wherein $R_2$ is an onium radical Z of formula (III)

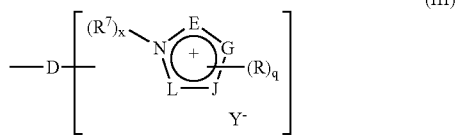

(III)

wherein:
D is a linker arm chosen from a covalent bond and from linear and branched $C_1$–$C_{14}$ alkylene chains that may optionally comprise at least one hetero atom chosen from oxygen, sulphur and nitrogen, and that may be optionally substituted with at least one radical chosen from hydroxyl and amino radicals, and that may further optionally comprise at least one carbonyl radical;
the ring members E, G, J and L, which may be identical or different, are chosen from carbon, oxygen, sulphur and nitrogen atoms to form a ring chosen from pyrrole, pyrazole, imidazole, triazole, oxazole, isooxazole, thiazole and isothiazole rings,
q is an integer ranging from 1 to 4;
R, which may be identical or different, is chosen from a hydrogen atom, halogen atoms, hydroxyl radicals, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, carbamoyl radicals, carboxyl radicals, $C_1$–$C_6$ alkylcarbonyl radicals, amino radicals, amino radicals mono- and disubstituted with a radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ monohydroxyalkyl radicals $C_2$–$C_6$ polyhydroxyalkyl radicals, and quaternary ammonium radicals;
$R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals, $C_1$–$C_6$ aminoalkyl radicals wherein the amine is substituted with a radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ carboxyalkyl radicals; $C_1$–$C_6$ carbamoylalkyl radicals; $C_1$–$C_6$ trifluoroalkyl radicals; tri($C_1$–$C_6$)alkylsilane($C_1$–$C_6$)alkyl radicals; $C_1$–$C_6$ sulphonamidoalkyl radicals; ($C_1$–$C_6$)alkylcarboxy($C_1$–$C_6$)alkyl radicals; ($C_1$–$C_6$)-alkylsulphinyl($C_1$–$C_6$)alkyl radicals; ($C_1$–$C_6$)alkylsulphonyl($C_1$–$C_6$)alkyl radicals; ($C_1$–$C_6$)alkylcarboxy($C_1$–$C_6$)alkyl radicals; N—($C_1$–$C_6$)alkylcarbamoyl($C_1$–$C_6$)alkyl radicals; N—($C_1$–$C_6$)alkylsulphonamido($C_1$–$C_6$)alkyl radicals; and quaternary ammonium radicals;
x is equal to 0 or 1, with the proviso that
when x=0, the linker arm D is attached to the nitrogen atom,
when x=1, the linker arm D is attached to one of the ring members E, G, J or L, and
$Y^-$ is a counterion.

11. The compound according to claim 10, wherein the ring members E, G, J and L form a ring chosen from pyrrole, imidazole, pyrazole, oxazole, thiazole and triazole rings.

12. The compound according to claim 11, wherein the ring members E, G, J and L form an imidazole ring.

13. The compound according to claim 10, wherein x is equal to 0 and D is chosen from a covalent bond and an alkylene chain that may be optionally substituted and/or that may optionally comprise a carbonyl function.

14. The compound according to claim 10, wherein x is equal to 0 and R is chosen from a hydrogen atom, hydroxyl radicals, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, carbamoyl radicals, $C_1$–$C_6$ alkylcarbonyl radicals, amino radicals, amino radicals mono- and disubstituted with at least one radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ monohydroxyalkyl radicals and $C_2$–$C_6$ polyhydroxyalkyl radicals.

15. The compound according to claim 10, wherein
x is equal to 1,
$R_7$ is chosen from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals; $C_1$–$C_6$ aminoalkyl radicals wherein the amine is mono- or disubstituted with at least one radical chosen from ($C_1$–$C_6$)alkyl radicals, ($C_1$–$C_6$)alkylcarbonyl radicals, carbamoyl radicals and ($C_1$–$C_6$)alkylsulphonyl radicals; $C_1$–$C_6$ carbamoylalkyl radicals; tri($C_1$–$C_6$)alkylsilane($C_1$–$C_6$)alkyl radicals; ($C_1$–$C_6$)alkylcarbonyl($C_1$–$C_6$)alkyl radicals; N—($C_1$–$C_6$)alkylcarbamyl($C_1$–$C_6$)alkyl radicals; and R is chosen from a hydrogen atom, a hydroxyl radical, $C_1$–$C_6$ alkyl radicals, $C_1$–$C_6$ monohydroxyalkyl radicals; $C_2$–$C_6$ polyhydroxyalkyl radicals, $C_1$–$C_6$ alkoxy radicals; tri($C_1$–$C_6$)alkylsilane($C_1$–$C_6$)alkyl radicals; carbamoyl radicals; $C_1$–$C_6$ alkylcarbonyl radicals; amino radicals; amino radicals mono- and disubstituted with at least one radical chosen from ($C_1$–$C_6$)alkyl, ($C_1$–$C_6$)alkylcarbonyl, carbamoyl and ($C_1$–$C_6$)alkylsulphonyl radicals.

16. The compound according to claim 15, wherein R is chosen from a hydrogen atom and alkyl radicals that may optionally be substituted, and $R_7$ is an alkyl radical that may optionally be substituted.

17. The compound according to claim 16, wherein R is chosen from hydrogen; an alkyl radical; alkyl radicals substituted with at least one hydroxyl; alkyl radicals substituted with at least one amino; a carboxyl radical; a carbamoyl radical; an amino radical; and a hydroxyl radical.

18. The compound according to claim 17, wherein R is chosen from hydrogen; a hydroxyl radical; a methyl radical; an amino radical; a hydroxymethyl radical; and an aminomethyl radical.

19. The compound according to claim 1, wherein $R_2$ is an onium radical Z of formula (IV)

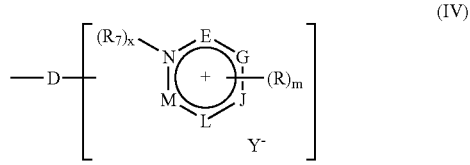

wherein:
D is a linker arm chosen from a covalent bond and from linear and branched $C_1$–$C_{14}$ alkylene chains, which may comprise at least one hetero atom chosen from oxygen, sulphur and nitrogen atoms, and which may optionally be substituted with at least one radical chosen from hydroxyl and amino radicals, and further may optionally comprise at least one carbonyl radical;
the ring members E, G, J, L and M, which may be identical or different, are chosen from carbon, oxygen, sulphur and nitrogen atoms and form a ring chosen from pyridine, pyrimidine, pyrazine, triazine and pyridazine rings;
m is an integer ranging from 1 to 5;
R, which may be identical or different, is chosen from a hydrogen atom, halogen atoms, hydroxyl radicals, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, carbamoyl radicals, carboxyl radicals, $C_1$–$C_6$ alkylcarbonyl radicals, amino radicals, amino radicals substituted with a radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ monohydroxy-alkyl radicals; $C_2$–$C_6$ polyhydroxyalkyl radicals; and quaternary ammonium radicals;
$R_7$ is chosen from $C_1$–$C_6$ alkyl radicals; $C_1$–$C_6$ monohydroxyalkyl radicals; $C_2$–$C_6$ polyhydroxyalkyl radicals; aryl radicals; benzyl radicals; $C_1$–$C_6$ aminoalkyl radicals; $C_1$–$C_6$ aminoalkyl radicals wherein the amine is mono- or disubstituted with at least one radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ carboxyalkyl radicals; $C_1$–$C_6$ carbamoylalkyl radicals; $C_1$–$C_6$ trifluoroalkyl radicals; tri($C_1$–$C_6$)alkylsilane($C_1$–$C_6$) alkyl radicals; $C_1$–$C_6$ sulphonamidoalkyl radicals; ($C_1$–$C_6$)alkylcarboxy($C_1$–$C_6$)alkyl radicals; ($C_1$–$C_6$)alkylsulphinyl($C_1$–$C_6$)alkyl radicals; ($C_1$–$C_6$)alkylsulphonyl($C_1$–$C_6$)alkyl radicals; ($C_1$–$C_6$)alkylcarboxy($C_1$–$C_6$)alkyl radicals; N—($C_1$–$C_6$)alkylcarbamoyl($C_1$–$C_6$)alkyl radicals; N—($C_1$–$C_6$)alkylsulphonamido($C_1$–$C_6$)alkyl radicals; and quaternary ammonium radicals;
x is equal to 0 or 1, with the proviso that
when x=0, the linker arm D is attached to the nitrogen atom,
when x=1, the linker arm D is attached to one of the ring members chosen from E, G, J, L and M; and
$Y^-$ is a counterion.

20. The compound according to claim 19, wherein the ring members E, G, J, L and M form, with the nitrogen of the ring, a ring chosen from pyridine and pyrimidine rings.

21. The compound according to claim 19, wherein
x is equal to 0, and
R is chosen from a hydrogen atom, hydroxyl radicals, $C_1$–$C_6$ alkyl radicals, $C_1$–$C_6$ monohydroxyalkyl radicals, $C_2$–$C_6$ polyhydroxyalkyl radicals, $C_1$–$C_6$ alkoxy radicals, tri($C_1$–$C_6$)alkylsilane($C_1$–$C_6$)alkyl radicals, carbamoyl radicals, $C_1$–$C_6$ alkylcarbonyl radicals, amino radicals, amino radicals mono- and disubstituted with at least one radical chosen from ($C_1$–$C_6$)alkyl, ($C_1$–$C_6$)alkylcarbonyl, carbamoyl and ($C_1$–$C_6$)alkylsulphonyl radicals; $C_1$–$C_6$ monohydroxyalkyl radicals and $C_2$–$C_6$ polyhydroxyalkyl radicals.

22. The compound according to claim 19, wherein
x is equal to 1;
$R_7$ is chosen from $C_1$–$C_6$ alkyl radicals; $C_1$–$C_6$ monohydroxyalkyl radicals; $C_2$–$C_6$ polyhydroxyalkyl radicals; $C_1$–$C_6$ aminoalkyl radicals, $C_1$–$C_6$ aminoalkyl radicals wherein the amine is mono- or disubstituted with at least one radical chosen from ($C_1$–$C_6$)alkyl radicals, ($C_1$–$C_6$)alkylcarbonyl radicals, carbamoyl radicals, and ($C_1$–$C_6$)alkylsulphonyl radicals; $C_1$–$C_6$ carbamoylalkyl radicals; tri($C_1$–$C_6$)alkylsilane($C_1$–$C_6$)alkyl radicals; ($C_1$–$C_6$)alkylcarbonyl($C_1$–$C_6$)alkyl radicals; N—($C_1$–$C_6$)alkylcarbamyl($C_1$–$C_6$)alkyl radicals; and
R is chosen from a hydrogen atom, hydroxyl radicals, $C_1$–$C_6$ alkyl radicals; $C_1$–$C_6$ monohydroxyalkyl radicals; $C_2$–$C_6$ polyhydroxyalkyl radicals; $C_1$–$C_6$ alkoxy radicals; tri($C_1$–$C_6$)alkylsilane($C_1$–$C_6$)alkyl radicals; carbamoyl radicals; $C_1$–$C_6$ alkylcarbonyl radicals; amino radicals; amino radicals mono- or disubstituted with at least one radical chosen from ($C_1$–$C_6$)alkyl, ($C_1$–$C_6$)alkylcarbonyl, carbamoyl and ($C_1$–$C_6$)alkylsulphonyl radicals.

23. The compound according to claim 22, wherein R is chosen from a hydrogen atom and alkyl radicals that may optionally be substituted, and $R_7$ is an alkyl radical that may optionally be substituted.

24. The compound according to claim 23, wherein R is chosen from hydrogen; an alkyl radical; alkyl radicals substituted with at least one hydroxyl; alkyl radicals substituted with at least one amino; a carboxyl radical; a carbamoyl radical; an amino radical; and a hydroxyl radical.

25. The compound according to claim 24, wherein R is chosen from hydrogen and from at least one radical chosen from hydroxyl, methyl, amino, hydroxymethyl and aminomethyl radicals.

26. The compound according to claim 1, wherein either b is equal to zero, or $R_4$ is chosen from an alkyl radical; alkyl radicals substituted with at least one hydroxyl; alkyl radicals substituted with at least one amino; a carboxyl radical; and a carbamoyl radical.

27. The compound according to claim 1, wherein $R_3$ is chosen from hydrogen; a hydroxyl radical; an amino radical; an alkyl radical; alkyl radicals substituted with at least one hydroxyl; alkyl radicals substituted with at least one amino; a carboxyl radical; and a carbamoyl radical.

28. The compound according to claim 1, wherein counterion $Y^-$ is chosen from halogens, a hydroxide, a hydrogen sulphate, an acetate, a tartrate and $(C_1–C_6)$alkyl sulphates.

29. The compound according to claim 1, chosen from the following compounds

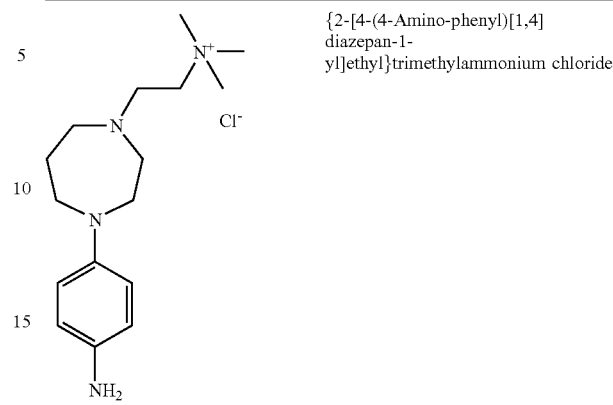

-continued

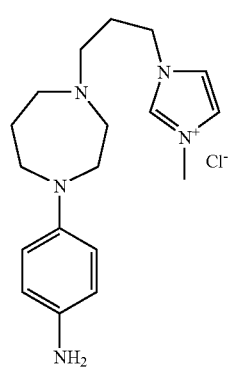
3-{2-[4-(4-Amino-phenyl)[1,4]diazepan-1-yl]propyl}-1-methyl-3H-imidazol-1-ium chloride

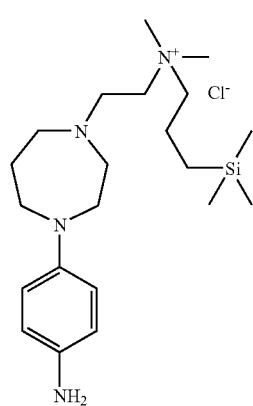
{2-[4-(4-Amino-phenyl)[1,4]diazepan-1-yl]ethyl}dimethyl-(3-trimethylsilanyl-propyl)ammonium; chloride

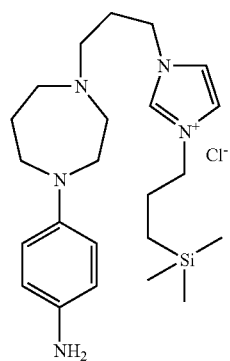
3-{2-[4-(4-Amino-phenyl)[1,4]diazepan-1-yl]ethyl}-1-(3-trimethylsilanyl-propyl)-3H-imidazol-1-ium chloride

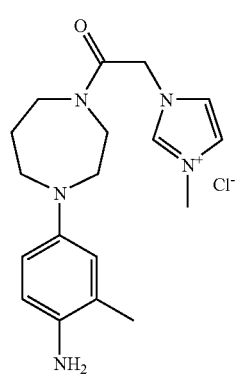
3-{2-[4-(4-Amino-3-methylphenyl)[1,4]-diazepan-1-yl]-2-oxoethyl}-1-methyl-3H-imidazol-1-ium chloride -continued

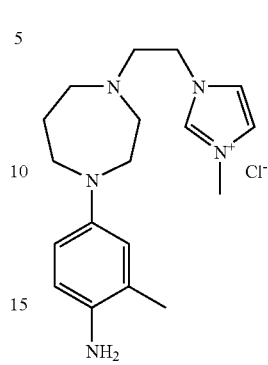
3-{2-[4-(4-Amino-3-methylphenyl)[1,4]-diazepan-1-yl]ethyl}-1-methyl-3H-imidazol-1-ium chloride

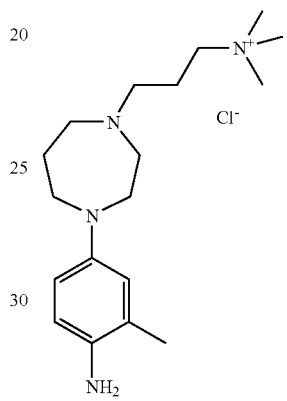
{3-[4-(4-Amino-3-methylphenyl)[1,4]-diazepan-1-yl]-propyl}trimethylammonium chloride

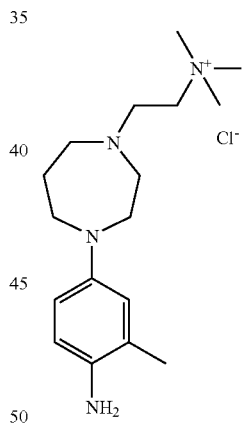
{2-[4-(4-Amino-3-methylphenyl)[1,4]diazepan-1-yl]ethyl}-trimethylammonium chloride

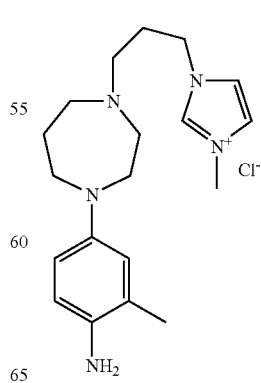
{3-[4-(4-Amino-3-methylphenyl)[1,4]-diazepan-1-yl]-propyl}-1-methyl-3H-imidazol-1-ium chloride -continued

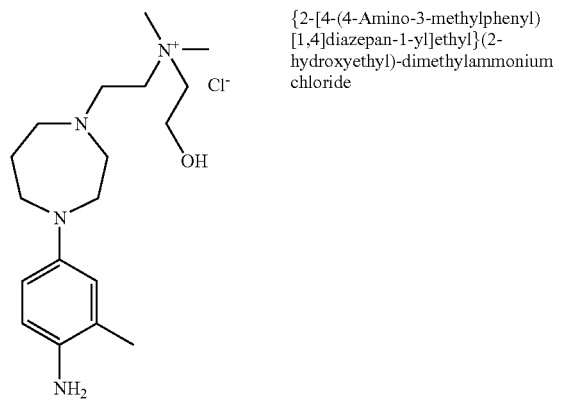
{2-[4-(4-Amino-3-methylphenyl)[1,4]diazepan-1-yl]ethyl}(2-hydroxyethyl)-dimethylammonium chloride

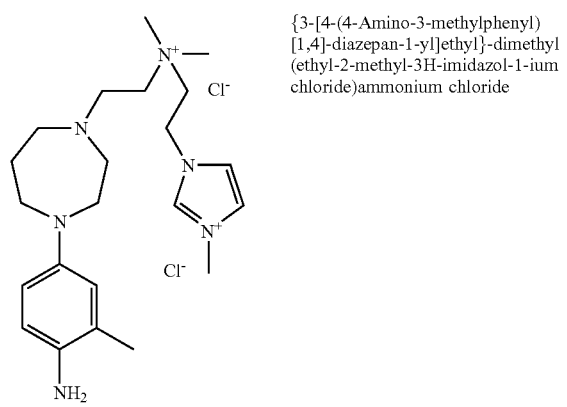
{3-[4-(4-Amino-3-methylphenyl)[1,4]-diazepan-1-yl]ethyl}-dimethyl(ethyl-2-methyl-3H-imidazol-1-ium chloride)ammonium chloride

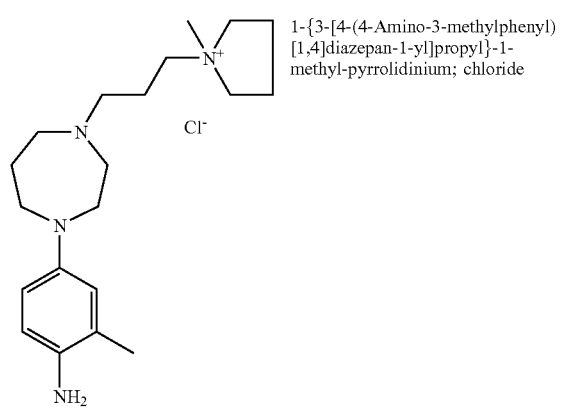
1-{3-[4-(4-Amino-3-methylphenyl)[1,4]diazepan-1-yl]propyl}-1-methyl-pyrrolidinium; chloride

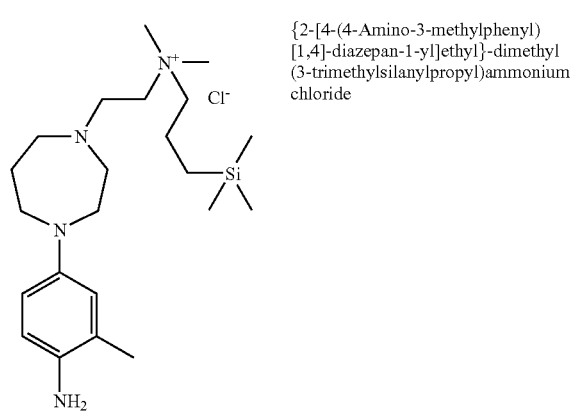
{2-[4-(4-Amino-3-methylphenyl)[1,4]-diazepan-1-yl]ethyl}-dimethyl(3-trimethylsilanylpropyl)ammonium chloride -continued

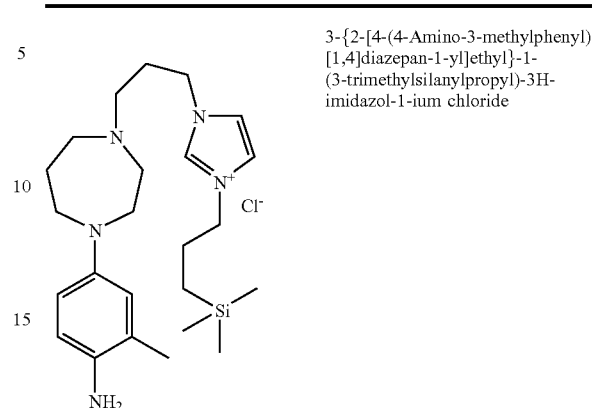
3-{2-[4-(4-Amino-3-methylphenyl)[1,4]diazepan-1-yl]ethyl}-1-(3-trimethylsilanylpropyl)-3H-imidazol-1-ium chloride

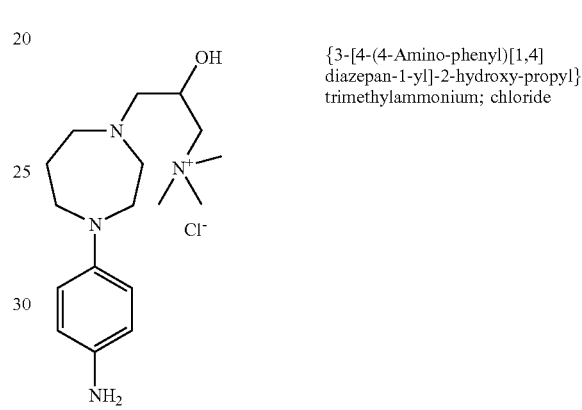
{3-[4-(4-Amino-phenyl)[1,4]diazepan-1-yl]-2-hydroxy-propyl}trimethylammonium; chloride

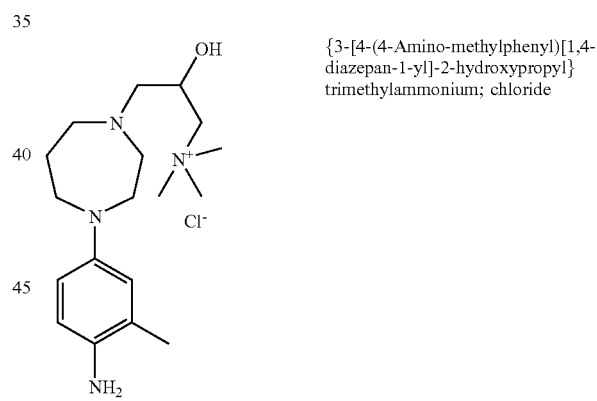
{3-[4-(4-Amino-methylphenyl)[1,4-diazepan-1-yl]-2-hydroxypropyl}trimethylammonium; chloride

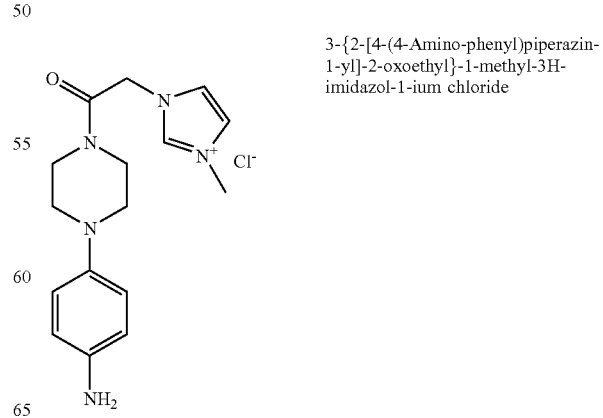
3-{2-[4-(4-Amino-phenyl)piperazin-1-yl]-2-oxoethyl}-1-methyl-3H-imidazol-1-ium chloride -continued

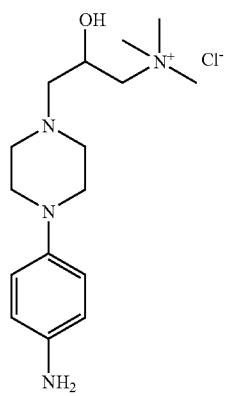

{3-[4-(4-Amino-phenyl)piperazin-1-yl]-2-hydroxypropyl} trimethylammonium chloride

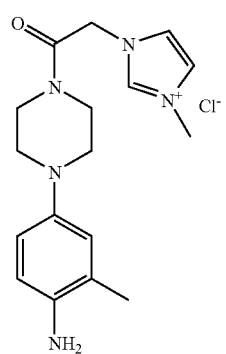

3-{2-[4-(4-Amino-3-methylphenyl) piperazin-1-yl]-2-oxoethyl}-1-methyl-3H-imidazol-1-ium chloride

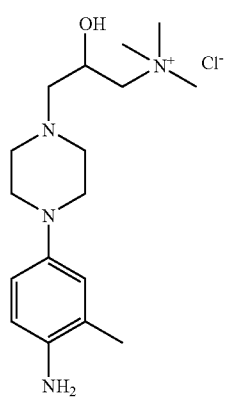

3-[4-(4-Amino-3-methylphenyl) piperazin-1-yl]-2-hydroxypropyl}-trimethylammonium chloride

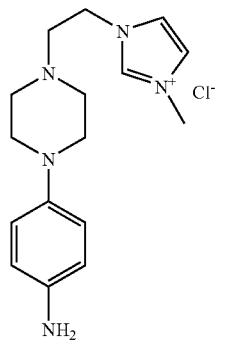

3-{2-[4-(4-Amino-3-phenyl) piperazin-1-yl]ethyl}-1-methyl-3H-imidazol-1-ium chloride -continued

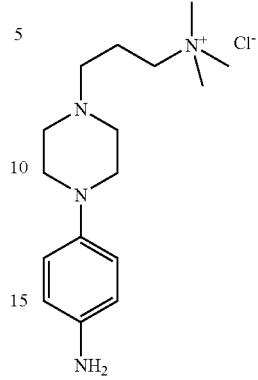

{3-[4-(4-Amino-3-phenyl) piperazin-1-yl]propyl} trimethylammonium chloride

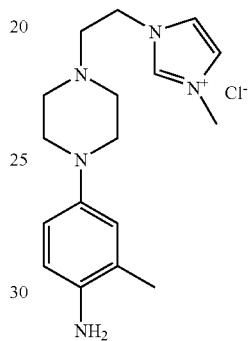

3-{2-[4-(4-Amino-3-methylphenyl) piperazin-1-yl]ethyl}-1-methyl-3H-imidazol-1-ium chloride

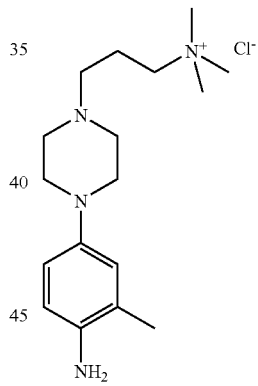

{3-[4-(4-Amino-3-methylphenyl) piperazin-1-yl]-propyl} trimethylammonium chloride

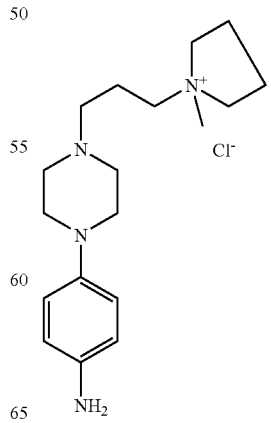

1-{3-[4-(4-Amino-phenyl) piperazin-1-yl]propyl}-1-methylpyrrolidinium chloride

-continued

1-{3-[4-(4-Amino-3-phenyl)piperazin-1-yl]propyl}-1-methylpyrrolidinium chloride

30. The nitro derivatives of formula (I')

(I')

wherein:
- a ranges from 0 to 4, it being understood that when a is greater than or equal to 2, then the radicals $R_1$ may be identical or different,
- b ranges from 0 to 4, it being understood that when b is greater than or equal to 2, then the radicals $R_4$ may be identical or different,
- c is equal to 0 or 1,
- $R_1$ is chosen from halogen atoms; $C_1$–$C_8$ aliphatic and alicyclic, saturated and unsaturated hydrocarbon-based chains, wherein at least one carbon atom is optionally replaced with at least one entity chosen from oxygen, nitrogen, silicon, and sulphur atoms and an $SO_2$ group; and an onium radical Z; with the proviso that the radical $R_1$ does not comprise a peroxide bond or diazo, nitro or nitroso radicals,
- $R_2$ comprises an onium radical Z, wherein an onium radical is a nitrogen-based quaternary radical,
- $R_3$ is chosen from
  - an alkyl radical;
  - an alkenyl radical;
  - an alkynyl radical;
  - a hydroxyl radical;
  - a hydroxyalkyl radical;
  - an alkoxy radical;
  - an alkoxyalkyl radical;
  - an alkylcarbonyl radical;
  - a hydroxyalkoxyalkyl radical;
  - an amino radical;
  - a monoalkylamino radical;
  - a dialkylamino;
  - an aminoalkyl radical;
  - an aminoalkyl radical wherein the amine is monosubstituted or disubstituted with at least one radical chosen from alkyl, acetyl and hydroxyalkyl radicals;
  - a hydroxyl radical;
  - a aminoalkyl radical;
  - a carboxyl radical;
  - a carboxyalkyl radical;
  - a carbamoyl radical;
  - a carbamoylalkyl radical;
  - an alkoxycarbonyl radical;
  - a monoalkylaminocarbonyl radical;
  - a dialkylaminocarbonyl radical;
  - a monoalkylaminocarbonylalkyl radical; and
  - a dialkylaminocarbonylalkyl radical;
- $R_4$ is chosen from
  - an alkyl radical;
  - an alkenyl radical;
  - an alkynyl radical;
  - a hydroxyalkyl radical;
  - an alkoxyalkyl radical;
  - an alkylcarbonyl radical;
  - a hydroxyalkoxyalkyl radical;
  - an aminoalkyl radical;
  - an aminoalkyl radical wherein the amine is monosubstituted or disubstituted with at least one radical chosen from alkyl, acetyl and hydroxyalkyl radicals;
  - a hydroxyl radical;
  - a aminoalkyl radical;
  - a carboxyl radical;
  - a carboxyalkyl radical;
  - a carbamoyl radical;
  - a carbamoylalkyl radical;
  - an alkoxycarbonyl radical;
  - a monoalkylaminocarbonyl radical;
  - a dialkylaminocarbonyl radical;
  - a monoalkylaminocarbonylalkyl radical; and
  - a dialkylaminocarbonylalkyl radical.

31. A dye composition comprising, as oxidation base, at least one compound of formula (I), and the addition salts thereof (I)

wherein:
- a ranges from 0 to 4, it being understood that when a is greater than or equal to 2, then the radicals $R_1$ may be identical or different,
- b ranges from 0 to 4, it being understood that when b is greater than or equal to 2, then the radicals $R_4$ may be identical or different,
- c is equal to 0 or 1, R$_1$ is chosen from halogen atoms; C$_1$–C$_8$ aliphatic and alicyclic, saturated and unsaturated hydrocarbon-based chains, wherein at least one carbon atom is optionally replaced with at least one entity chosen from oxygen, nitrogen, silicon, and sulphur atoms and an SO$_2$ group; and an onium radical Z; with the proviso that the radical R$_1$ does not comprise a peroxide bond or diazo, nitro or nitroso radicals, R$_2$ comprises an onium radical Z, wherein an onium radical is a nitrogen-based quaternary radical, R$_3$ is chosen from
- an alkyl radical;
- an alkenyl radical;
- an alkynyl radical;
- a hydroxyl radical;
- a hydroxyalkyl radical;
- an alkoxy radical;
- an alkoxyalkyl radical;
- an alkylcarbonyl radical;
- a hydroxyalkoxyalkyl radical;
- an amino radical;
- a monoalkylamino radical;
- a dialkylamino;
- an aminoalkyl radical;
- an aminoalkyl radical wherein the amine is monosubstituted or disubstituted with at least one radical chosen from alkyl, acetyl and hydroxyalkyl radicals;
- a hydroxyl radical;
- a aminoalkyl radical;
- a carboxyl radical;
- a carboxyalkyl radical;
- a carbamoyl radical;
- a carbamoylalkyl radical;
- an alkoxycarbonyl radical;
- a monoalkylaminocarbonyl radical;
- a dialkylaminocarbonyl radical;
- a monoalkylaminocarbonylalkyl radical; and
- a dialkylaminocarbonylalkyl radical;

R$_4$ is chosen from
- an alkyl radical;
- an alkenyl radical;
- an alkynyl radical;
- a hydroxyalkyl radical;
- an alkoxyalkyl radical;
- an alkylcarbonyl radical;
- a hydroxyalkoxyalkyl radical;
- an aminoalkyl radical;
- an aminoalkyl radical wherein the amine is monosubstituted or disubstituted with at least one radical chosen from alkyl, acetyl and hydroxyalkyl radicals;
- a hydroxyl radical;
- a aminoalkyl radical;
- a carboxyl radical;
- a carboxyalkyl radical;
- a carbamoyl radical;
- a carbamoylalkyl radical;
- an alkoxycarbonyl radical;
- a monoalkylaminocarbonyl radical;
- a dialkylaminocarbonyl radical;
- a monoalkylaminocarbonylalkyl radical; and
- a dialkylaminocarbonylalkyl radical.

32. The dye composition according to claim 31, further comprising at least one coupler chosen from meta-phenylenediamines, meta-aminophenols, meta-diphenols, naphthalene-based couplers, heterocyclic couplers, and the addition salts thereof.

33. The composition according to claim 31, comprising at least one additional oxidation base other than the compound of formula (I), chosen from para-phenylenediamines, bis (phenyl)alkylenediamines, para-aminophenols, ortho-aminophenols, heterocyclic bases, and the addition salts thereof.

34. The composition according to claim 33, wherein, for the at least one compound of formula (I) and for the at least one additional oxidation base, if present, each oxidation base in the dye composition is present in an amount ranging from about 0.001% to about 10% by weight, relative to the total weight of the dye composition.

35. The dye composition according to claim 32, wherein the at least one coupler is present in the dye composition in an amount ranging from about 0.001% to about 10% by weight, relative to the total weight of the dye composition.

36. The dye composition according to claim 31, further comprising a cosmetic medium suitable for dyeing keratin fibers.

37. A process for the oxidation dyeing of keratin fibers, comprising applying a dye composition to the fibers in the presence of at least one oxidizing agent, for a time sufficient to develop a desired coloration, wherein the dye composition comprises, as an oxidation base, at least one compound of formula (I), and the addition salts thereof

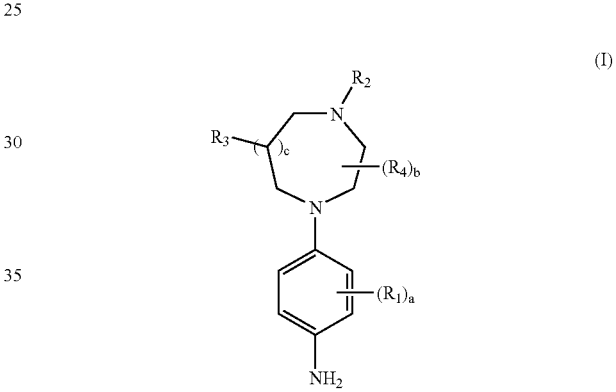

wherein:
- a ranges from 0 to 4, it being understood that when a is greater than or equal to 2, then the radicals R$_1$ may be identical or different,
- b ranges from 0 to 4, it being understood that when b is greater than or equal to 2, then the radicals R$_4$ may be identical or different,
- c is equal to 0 or 1,
- R$_1$ is chosen from halogen atoms; C$_1$–C$_8$ aliphatic and alicyclic, saturated and unsaturated hydrocarbon-based chains, wherein at least one carbon atom is optionally replaced with at least one entity chosen from oxygen, nitrogen, silicon, and sulphur atoms and an SO$_2$ group; and an onium radical Z; with the proviso that the radical R$_1$ does not comprise a peroxide bond or diazo, nitro or nitroso radicals,
- R$_2$ comprises an onium radical Z, wherein an onium radical is a nitrogen-based quaternary radical,
- R$_3$ is chosen from
  - an alkyl radical;
  - an alkenyl radical;
  - an alkynyl radical;
  - a hydroxyl radical;
  - a hydroxyalkyl radical;
  - an alkoxy radical;
  - an alkoxyalkyl radical;

an alkylcarbonyl radical;
a hydroxyalkoxyalkyl radical;
an amino radical;
a monoalkylamino radical;
a dialkylamino;
an aminoalkyl radical;
an aminoalkyl radical wherein the amine is monosubstituted or disubstituted with at least one radical chosen from alkyl, acetyl and hydroxyalkyl radicals;
a hydroxyl radical;
a aminoalkyl radical;
a carboxyl radical;
a carboxyalkyl radical;
a carbamoyl radical;
a carbamoylalkyl radical;
an alkoxycarbonyl radical;
a monoalkylaminocarbonyl radical;
a dialkylaminocarbonyl radical;
a monoalkylaminocarbonylalkyl radical; and
a dialkylaminocarbonylalkyl radical;

$R_4$ is chosen from
an alkyl radical;
an alkenyl radical;
an alkynyl radical;
a hydroxyalkyl radical;
an alkoxyalkyl radical;
an alkylcarbonyl radical;
a hydroxyalkoxyalkyl radical;
an aminoalkyl radical;
an aminoalkyl radical wherein the amine is monosubstituted or disubstituted with at least one radical chosen from alkyl, acetyl and hydroxyalkyl radicals;
a hydroxyl radical;
a aminoalkyl radical;
a carboxyl radical;
a carboxyalkyl radical;
a carbamoyl radical;
a carbamoylalkyl radical;
an alkoxycarbonyl radical;
a monoalkylaminocarbonyl radical;
a dialkylaminocarbonyl radical;
a monoalkylaminocarbonylalkyl radical; and
a dialkylaminocarbonylalkyl radical.

38. The process according to claim 37, wherein the at least one oxidizing agent is chosen from hydrogen peroxide, urea peroxide, alkali metal bromates, persalts, peracids and oxidase enzymes.

39. The process according to claim 37, wherein the at least one oxidizing agent may be added to the dye composition at the time of application to the fibers or it may be applied in the form of an oxidizing composition simultaneously or sequentially with the application of the dye composition.

40. A multi-compartment kit, wherein at least one first compartment comprises a dye composition comprising, as an oxidation base, at least one compound of formula (I), and the addition salts thereof

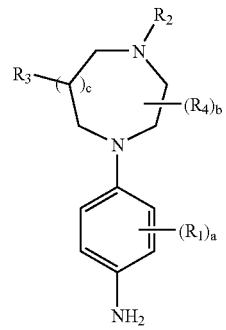

(I)

wherein:
a ranges from 0 to 4, it being understood that when a is greater than or equal to 2, then the radicals $R_1$ may be identical or different,
b ranges from 0 to 4, it being understood that when b is greater than or equal to 2, then the radicals $R_4$ may be identical or different,
c is equal to 0 or 1,
$R_1$ is chosen from halogen atoms; $C_1$–$C_8$ aliphatic and alicyclic, saturated and unsaturated hydrocarbon-based chains, wherein at least one carbon atom is optionally replaced with at least one entity chosen from oxygen, nitrogen, silicon, and sulphur atoms and an $SO_2$ group; and an onium radical Z; with the proviso that the radical $R_1$ does not comprise a peroxide bond or diazo, nitro or nitroso radicals,
$R_2$ comprises an onium radical Z, wherein an onium radical is a nitrogen-based quaternary radical,
$R_3$ is chosen from
an alkyl radical;
an alkenyl radical;
an alkynyl radical;
a hydroxyl radical;
a hydroxyalkyl radical;
an alkoxy radical;
an alkoxyalkyl radical;
an alkylcarbonyl radical;
a hydroxyalkoxyalkyl radical;
an amino radical;
a monoalkylamino radical;
a dialkylamino;
an aminoalkyl radical;
an aminoalkyl radical wherein the amine is monosubstituted or disubstituted with at least one radical chosen from alkyl, acetyl and hydroxyalkyl radicals;
a hydroxyl radical;
a aminoalkyl radical;
a carboxyl radical;
a carboxyalkyl radical;
a carbamoyl radical;
a carbamoylalkyl radical;
an alkoxycarbonyl radical;
a monoalkylaminocarbonyl radical;
a dialkylaminocarbonyl radical;
a monoalkylaminocarbonylalkyl radical; and
a dialkylaminocarbonylalkyl radical;

$R_4$ is chosen from
an alkyl radical;
an alkenyl radical;
an alkynyl radical;

a hydroxyalkyl radical;
an alkoxyalkyl radical;
an alkylcarbonyl radical;
a hydroxyalkoxyalkyl radical;
an aminoalkyl radical;
an aminoalkyl radical wherein the amine is monosubstituted or disubstituted with at least one radical chosen from alkyl, acetyl and hydroxyalkyl radicals;
a hydroxyl radical;
a aminoalkyl radical;
a carboxyl radical;
a carboxyalkyl radical;
a carbamoyl radical;
a carbamoylalkyl radical;
an alkoxycarbonyl radical;
a monoalkylaminocarbonyl radical;
a dialkylaminocarbonyl radical;
a monoalkylaminocarbonylalkyl radical; and
a dialkylaminocarbonylalkyl radical and at least one second compartment comprises at least one oxidizing agent.

* * * * *

UNITED STATES PATENT AND TRADEMARK OFFICE
CERTIFICATE OF CORRECTION

PATENT NO. : 7,090,703 B2
APPLICATION NO. : 10/807162
DATED : August 15, 2006
INVENTOR(S) : Stephane Sabelle It is certified that error appears in the above-identified patent and that said Letters Patent is hereby corrected as shown below:

In claim 1, column 33, line 8, "a aminoalkyl" should read --an aminoalkyl--.

In claim 1, column 33, line 31, "a aminoalkyl" should read --an aminoalkyl--.

In claim 10, column 35, lines 46-52,

"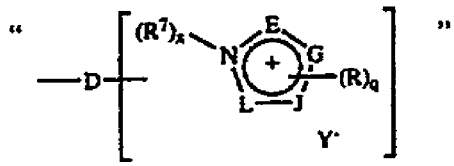"

should read

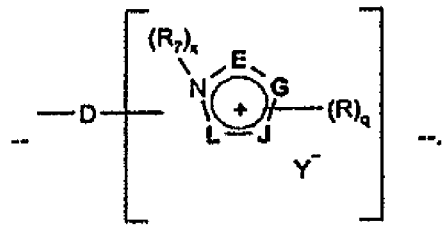

--.

In claim 29, column 39, lines 50-52, "3-{2-[4-(4-Amino-phenyl)[1,4]diazepan-1-yl]propyl}-trimethylammonium chloride" should read --{3-[4-(4-Amino--phenyl)[1,4]diazepan-1-yl]propyl}trimethylammonium chloride--.

In claim 29, column 40, lines 51-54, "{3-[4-(4-Amino-phenyl)[1,4]diazepan-1-yl]ethyl}dimethyl(ethyl-2-methyl-3H-imidazol-1-ium chloride)ammonium; chloride" should read --{3-[4-(4-Amino-phenyl)[1,4]diazepan-1-yl]ethyl}dimethyl(ethyl-2-methyl-3H-imidazol-1-ium chloride)ammonium chloride--.

In claim 29, column 41, lines 20-23, "{2-[4-(4-Amino-phenyl)[1,4]diazepan-1-yl]ethyl}dimethyl-(3-trimethylsilanyl-propyl)ammonium; chloride" should read --{2-[4-(4-Amino-phenyl)[1,4]diazepan-1-yl]ethyl}dimethyl-(3-trimethylsilanyl-propyl)ammonium chloride--.

UNITED STATES PATENT AND TRADEMARK OFFICE
CERTIFICATE OF CORRECTION

PATENT NO. : 7,090,703 B2
APPLICATION NO. : 10/807162
DATED : August 15, 2006
INVENTOR(S) : Stephane Sabelle It is certified that error appears in the above-identified patent and that said Letters Patent is hereby corrected as shown below:

In claim 29, column 41, lines 36-39, "3-{2-[4-(4-Amino-phenyl)[l,4]diazepan-l-yl]ethyl}-l-(3-trimethylsilanyl-propyl)-3H-imidazol-1-ium chloride" should read --3-{2-[4-(4-Amino-phenyl)[1,4]diazepan-l-yl]ethyl}-1-(3-trimethylsilanylpropyl)-3H-imidazol-l-ium chloride--.

In claim 29, column 42, lines 52-54, "{3-{4-(4-Amino-3-methylphenyl)[1,4]-diazepan-1-yl]-propyl}-1-methyl-3H-imidazol-1-ium chloride" should read --3-{2-[4-(4-Amino-3-methylphenyl)[1,4]-diazepan-1-yl]propyl}-l-methyl-3H-imidazol-l-ium chloride--.

In claim 29, column 43, lines 35-37, "1-{3-[4-(4-Amino-3-methylphenyl)[1,4]diazepan-1-yl]propyl}-1-methyl-pyrrolidinium; chloride" should read --1-{3-[4-(4-Amino-3-methylphenyl)[1,4]diazepan-1-yl]propyl}-l-methylpyrrolidinium chloride--.

In claim 29, column 44, lines 20-22, "{3-[4-(4-Amino-phenyl)[1,4]diazepan-1-yl]-2-hydroxy-propyl}trimethylammonium; chloride" should read --{3-[4-(4-Amino- phenyl)[1,4]diazepan-l-yl]-2-hydroxypropyl}trimethylammonium chloride--.

In claim 29, column 44, lines 36-38, "{3-[4-(4-Amino-methylphenyl)[l,4-diazepan-1-yl]-2-hydroxypropyl}trimethylammonium; chloride" should read --{3-[4-(4-Amino-3-methylphenyl)[1,4-diazepan-1-yl]-2-hydroxypropyl}trimethylammonium chloride--.

In claim 29, column 45, lines 51-53, "3-{2-[4-(4-Amino-3-phenyl)piperazin-1-yl]ethyl}-1-methyl-3H-imidazol-l-ium chloride" should read --3-{2-[4-(4-Amino-phenyl)piperazin-1-yl]ethyl}-1-methyl-3H-imidazol-1-ium chloride--.

In claim 29, column 46, lines 1-3, "{3-[4-(4-Amino-3-phenyl)piperazin-1-yl]propyl}trimethylammonium chloride" should read --{3-[4-(4-Amino-phenyl)piperazin-1-yl]propyl}trimethylammonium chloride--.

In claim 29, column 46, lines 34-36, "{3-[4-(4-Amino-3-methylphenyl)piperazin-1-yl]-propyl}trimethylammonium chloride" should read --{3-[4-(4-Amino-3- methylphenyl)piperazin-1-yl]propyl}trimethylammonium chloride--.

In claim 29, column 47, lines 3-5, "1-{3-[4-(4-Amino-3-phenyl)piperazin-1-yl}propyl}-l-methylpyrrolidinium chloride" should read --1-{3-[4-(4-Amino-3-methylphenyl)piperazin-i-yl]propyl}-1-methylpyrrolidinium chloride--.

UNITED STATES PATENT AND TRADEMARK OFFICE
CERTIFICATE OF CORRECTION

PATENT NO.       : 7,090,703 B2
APPLICATION NO.  : 10/807162
DATED            : August 15, 2006
INVENTOR(S)      : Stephane Sabelle It is certified that error appears in the above-identified patent and that said Letters Patent is hereby corrected as shown below:

In claim 30, column 48, line 7, "a aminoalkyl" should read --an aminoalkyl--.

In claim 30, column 48, line 30, "a aminoalkyl" should read --an aminoalkyl--.

In claim 31, column 49, line 29, "a aminoalkyl" should read --an aminoalkyl--.

In claim 31, column 49, line 53, "a aminoalkyl" should read --an aminoalkyl--.

In claim 37, column 51, line 13, "a aminoalkyl" should read --an aminoalkyl--.

In claim 37, column 51, line 41, "a aminoalkyl" should read --an aminoalkyl--.

In claim 40, column 52, line 53, "a aminoalkyl" should read --an aminoalkyl--.

In claim 40, column 53, line 10, "a aminoalkyl" should read --an aminoalkyl--.

Signed and Sealed this

Ninth Day of January, 2007

JON W. DUDAS
*Director of the United States Patent and Trademark Office*